(12) United States Patent
Kasper et al.

(10) Patent No.: US 8,206,726 B2
(45) Date of Patent: Jun. 26, 2012

(54) ZWITTERIONIC POLYSACCHARIDES FOR PROMOTION OF IMMUNE SYSTEM MATURATION AND HEALTH

(75) Inventors: Dennis L. Kasper, Brookline, MA (US); Sarkis K. Mazmanian, Porter Ranch, CA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 242 days.

(21) Appl. No.: 12/223,563

(22) PCT Filed: Feb. 5, 2007

(86) PCT No.: PCT/US2007/003160
§ 371 (c)(1),
(2), (4) Date: Apr. 3, 2009

(87) PCT Pub. No.: WO2007/092451
PCT Pub. Date: Aug. 16, 2007

(65) Prior Publication Data
US 2009/0317427 A1 Dec. 24, 2009

Related U.S. Application Data

(60) Provisional application No. 60/765,800, filed on Feb. 6, 2006.

(51) Int. Cl.
*A61K 39/38* (2006.01)
*A61K 39/02* (2006.01)
*A61K 39/07* (2006.01)
*A61K 45/00* (2006.01)
*A61K 47/00* (2006.01)

(52) U.S. Cl. ............... 424/278.1; 424/184.1; 424/234.1; 424/246.1; 424/244.1

(58) Field of Classification Search .................. None
See application file for complete search history.

(56) References Cited

U.S. PATENT DOCUMENTS

| | | | |
|---|---|---|---|
| 3,849,550 A | 11/1974 | Teitelbaum et al. | |
| 4,619,995 A | 10/1986 | Hayes | |
| 4,782,067 A | 11/1988 | Blythin et al. | |
| 4,819,617 A | 4/1989 | Goldberg et al. | |
| 4,835,252 A | 5/1989 | Musso et al. | |
| 4,886,787 A | 12/1989 | de Belder et al. | |
| 4,937,270 A | 6/1990 | Hamilton et al. | |
| 5,126,141 A | 6/1992 | Henry | |
| 5,130,417 A | 7/1992 | Stanley et al. | |
| 5,140,016 A | 8/1992 | Goldberg et al. | |
| 5,158,939 A | 10/1992 | Takayama et al. | |
| 5,196,510 A | 3/1993 | Rodwell et al. | |
| 5,215,896 A | 6/1993 | Keck et al. | |
| 5,331,573 A | 7/1994 | Balaji et al. | |
| 5,514,581 A | 5/1996 | Ferrari et al. | |
| 5,532,221 A | 7/1996 | Huang et al. | |
| 5,576,002 A | 11/1996 | Jennings et al. | |
| 5,605,938 A | 2/1997 | Roufa et al. | |
| 5,679,654 A | 10/1997 | Tzianabos et al. | |
| 5,679,658 A | 10/1997 | Elson | |
| 5,700,787 A | 12/1997 | Tzianabos et al. | |
| 5,700,906 A | 12/1997 | Arnot et al. | |
| 5,705,178 A | 1/1998 | Roufa et al. | |
| 5,760,200 A | 6/1998 | Miller et al. | |
| 5,888,741 A | 3/1999 | Hendry | |
| 5,993,825 A * | 11/1999 | Jennings et al. ............ 424/244.1 |
| 6,110,672 A | 8/2000 | Mandel et al. | |
| 6,150,459 A | 11/2000 | Mayes et al. | |
| 6,294,518 B1 | 9/2001 | Potter et al. | |
| 6,447,765 B1 | 9/2002 | Horwitz | |
| 6,995,237 B1 | 2/2006 | Zimmerman | |
| 7,026,285 B2 * | 4/2006 | Tzianabos et al. ............. 514/9.4 |
| 7,083,777 B1 * | 8/2006 | Tzianabos et al. ......... 424/9.322 |
| 7,163,683 B2 | 1/2007 | Barstad et al. | |
| 7,166,455 B2 * | 1/2007 | Comstock et al. ......... 435/252.1 |
| 7,629,330 B2 * | 12/2009 | Wang et al. ..................... 514/54 |
| 7,678,558 B2 * | 3/2010 | Comstock et al. ......... 435/252.1 |
| 7,803,602 B2 * | 9/2010 | Comstock et al. ......... 435/252.3 |
| 8,008,276 B2 * | 8/2011 | Wang et al. ..................... 514/54 |
| 2001/0001788 A1 | 5/2001 | Satoh et al. | |
| 2002/0090357 A1 | 7/2002 | Barrat et al. | |
| 2003/0219413 A1 | 11/2003 | Comstock et al. | |
| 2004/0092433 A1 * | 5/2004 | Wang et al. ........................ 514/8 |
| 2004/0219160 A1 * | 11/2004 | Tzianabos et al. ......... 424/184.1 |
| 2005/0119164 A1 | 6/2005 | Taylor et al. | |
| 2006/0153832 A1 | 7/2006 | Tzianabos et al. | |
| 2007/0020730 A1 | 1/2007 | Comstock et al. | |
| 2008/0057565 A1 * | 3/2008 | Comstock et al. ......... 435/252.3 |
| 2009/0124573 A1 * | 5/2009 | Mazmanian et al. ........... 514/54 |
| 2009/0317410 A1 | 12/2009 | Wang et al. | |
| 2009/0317427 A1 * | 12/2009 | Kasper et al. ............... 424/244.1 |
| 2010/0311686 A1 * | 12/2010 | Kasper et al. ................... 514/54 |
| 2011/0009360 A1 * | 1/2011 | Kasper et al. ................... 514/54 |
| 2011/0059125 A1 * | 3/2011 | Tzianabos et al. ........ 424/197.11 |
| 2011/0086011 A1 * | 4/2011 | Kasper et al. ............... 424/93.41 |

FOREIGN PATENT DOCUMENTS
DE  3704389 A1  8/1988
(Continued)

OTHER PUBLICATIONS

Kalka-Moll et al, J. Immunol., 2002, 169:6149-6153.* Comstock et al, Cell, Sep. 8, 2006, 126:847-850.*
Kalka-Moll et al, J Immunol 2002;169;6149-6153.*
Mazmanian et al, Nature Reviews/Immunology, Nov. 2006, 6:849-858.*
Mazmanian et al, Cell, vol. 122, 107-118, Jul. 15, 2005.*
GenBank Accession No. AJ277832; Hutloff Jan. 19, 2001.
GenBank Accession No. CAC06612; Hutloff Jan. 19, 2001.
GenBank Accession No. NM_012092; Dec. 20, 2003.
GenBank Accession No. NP_036224 Dec. 20, 2003.
NCBI Sequence View "Toxin" [*Salmonella typhimurium* LT2]. http://www.ncbi.nim.nih.gov/entrez/viewer.fcgi?db=protein&id=17233414, pp. 1-2.
No Author Listed, Acute Respiratory Disease Syndrome: What is acute respiratory disease syndrome? American Lung Association. 3 pages. http://www.lungusa.org/site/apps/nlnet/content3.aspz?c=dvLUK9O0E&b=2058817&content.

(Continued)

*Primary Examiner* — Nita M Minnifield
(74) *Attorney, Agent, or Firm* — Wolf, Greenfield & Sacks, P.C.

(57) ABSTRACT

Certain zwitterionic polysaccharides, including those naturally expressed by commensal *B. fragilis* in the gut, interact with cells of the immune system and affect the $T_H1/T_H2$ balance so as to promote health. Nutritional formulas and nutritional supplements containing isolated preparations of such zwitterionic polysaccharides, and methods for preparing the nutritional formulas and supplements, are provided. Also provided is a method of promoting immune system maturation in an infant involving enteral administration of a nutritional formula or nutritional supplement of the invention.

14 Claims, 12 Drawing Sheets

FOREIGN PATENT DOCUMENTS

| | | | |
|---|---|---|---|
| EP | 1358885 A1 | 11/2003 | |
| EP | 1459757 A1 | 9/2004 | |
| GB | 2286193 | 8/1995 | |
| JP | 56128721 | 10/1981 | |
| WO | WO 95/31990 A1 | 11/1995 | |
| WO | WO 96/07427 A1 | 3/1996 | |
| WO | WO 96/32119 A1 | 10/1996 | |
| WO | WO 96/35433 A1 | 11/1996 | |
| WO | WO 98/45335 A1 | 10/1998 | |
| WO | WO 00/001733 | 1/2000 | |
| WO | WO 00/59515 A2 | 10/2000 | |
| WO | WO 02/45708 A2 | 6/2002 | |
| WO | WO 02/45708 A3 | 6/2002 | * |
| WO | WO 03/075953 A2 | 9/2003 | |
| WO | WO 03/077863 A2 | 9/2003 | * |
| WO | WO 2004/089407 A2 | 10/2004 | * |
| WO | WO 2007/092451 A2 | 8/2007 | * |
| WO | WO 2009/062132 A2 | 5/2009 | * |

OTHER PUBLICATIONS

No Author Listed, Lupus study. Meet A Lupus Researcher. www.lupusstudy.org/updates.php. 2005;1-2.

No Author Listed, Polyethylene Glycols (PEGs). Accessed Mar. 7, 2005. 1 page. http://www.mindfully.org/Plastic/Polymers/Polyethylene-Glycols-PEGs.htm.

No Author Listed, The Merck Index. Eleventh Edition 1989:734-735.

No Author Listed, VAXA, Systemic lupus erythematosus (SLE), damaging and unpredictable. http://www.vaxa.com/arthritis-systemic-lupus-erythematosus.cfm. 1 page.

Aharoni et al., Bystander suppression of experimental autoimmune encephalomyelitis by T cell lines and clones of the Th2 type induced by copolymer 1. J Neuroimmunol. Nov. 2, 1998;91(1-2):135-46.

Aharoni et al., Copolymer 1 induces T cells of the T helper type 2 that crossreact with myelin basic protein and suppress experimental autoimmune encephalomyelitis. Proc Natl Acad Sci U S A. Sep. 30, 1997;94(20):10821-6.

Aharoni et al., Studies on the mechanism and specificity of the effect of the synthetic random copolymer GLAT on graft-versus-host disease. Immunol Lett. Jul. 1997;58(2):79-87.

Akbari et al., Antigen-specific regulatory T cells develop via the ICOS-ICOS-ligand pathway and inhibit allergen-induced airway hyperreactivity. Nat Med. Sep. 2002;8(9):1024-32. Epub Jul. 29, 2002.

Arnon et al., New insights into the mechanism of action of copolymer 1 in experimental allergic encephalomyelitis and multiple sclerosis. J Neurol. Apr. 1996;243(4 Suppl 1):S8-13. Review.

Barrat et al., In vitro generation of interleukin 10-producing regulatory CD4(+) T cells is induced by immunosuppressive drugs and inhibited by T helper type 1 (Th1)- and Th2-inducing cytokines. J Exp Med. Mar. 4, 2002;195(5):603-16.

Basu et al., Synthesis and characterization of a peptide nucleic acid conjugated to a D-peptide analog of insulin-like growth factor 1 for increased cellular uptake. Bioconjug Chem. Jul.-Aug. 1997;8(4):481-8.

Batta et al., Conformational stabilization of the altruronic acid residue in the O-specific polysaccharide of *Shigella sonnei/Plesiomonas shigelloides*. Carbohydr Res. Dec. 1997;305(1):93-9.

Baumann et al., Structural elucidation of two capsular polysaccharides from one strain of *Bacteroides fragilis* using high-resolution NMR spectroscopy. Biochemistry. Apr. 28, 1992;31(16):4081-9.

Bazan et al., Unraveling the structure of IL-2. Science. Jul. 17, 1992;257(5068):410-3.

Boes et al., Accelerated development of IgG autoantibodies and autoimmune disease in the absence of secreted IgM. Proc Natl Acad Sci U S A. Feb. 1, 2000;97(3):1184-9.

Brubaker et al., Mitogenic activity of purified capsular polysaccharide A from *Bacteroides fragilis*: differential stimulatory effect on mouse and rat lymphocytes in vitro. J Immunol. Feb. 15, 1999;162(4):2235-42.

Büdinger et al., Immunologic mechanisms in hypersensitivity reactions to metal ions: an overview. Allergy. Feb. 2000;55(2):108-15. Review.

Cobb et al., Zwitterionic capsular polysaccharides: the new MHCII-dependent antigens. Cell Microbiol. Oct. 2005;7(10):1398-403. Review.

Comstock et al., Interstrain variation of the polysaccharide B biosynthesis locus of *Bacteroides fragilis*: characterization of the region from strain 638R. J Bacteriol. Oct. 1999;181(19):6192-6.

Coyne et al., *Bacteroides fragilis* NCTC9343 produces at least three distinct capsular polysaccharides: cloning, characterization, and reassignment of polysaccharide B and C biosynthesis loci. Infect Immun. Nov. 2000;68(11):6176-81.

Crabb et al., T cell regulation of *Bacteroides fragilis*-induced intraabdominal abscesses. Rev Infect Dis. Jan.-Feb. 1990;12 Suppl 2:S178-84. Review.

Craig, Autologous hematopoietic stem cell transplantation for Crohn's disease. Autoimmun Rev. Aug. 2002;1(4):244-9. Review.

Dahiyat et al., De novo protein design: fully automated sequence selection. Science. Oct. 3, 1997;278(5335):82-7.

Di Fabio et al., Structure of the capsular polysaccharide antigen of type IV group B *Streptococcus*. Can J Cancer. 1989;67:877-882.

Finberg et al., Decay-accelerating factor expression on either effector or target cells inhibits cytotoxicity by human natural killer cells. J Immunol. Sep. 15, 1992;149(6):2055-60.

Fournier et al., Isolation of type 5 capsular polysaccharide from *Staphylococcus aureus*. Ann Inst Pasteur Microbiol. Sep.-Oct. 1987;138(5):561-7.

Fridkis-Hareli et al., Binding motifs of copolymer 1 to multiple sclerosis- and rheumatoid arthritis-associated HLA-DR molecules. J Immunol. Apr. 15, 1999;162(8):4697-704.

Fridkis-Hareli et al., Binding of random copolymers of three amino acids to class II MHC molecules. Int Immunol. May 1999;11(5):635-41.

Fridkis-Hareli et al., Direct binding of myelin basic protein and synthetic copolymer 1 to class II major histocompatibility complex molecules on living antigen-presenting cells—specificity and promiscuity. Proc Natl Acad Sci U S A. May 24, 1994;91(11):4872-6.

Fridkis-Hareli et al., Synthetic copolymer 1 and myelin basic protein do not require processing prior to binding to class II major histocompatibility complex molecules on living antigen-presenting cells. Cell Immunol. Jul. 1995;163(2):229-36.

Gibson et al., Cellular mechanism of intraabdominal abscess formation by *Bacteroides fragilis*. J Immunol. May 15, 1998;160(10):5000-6.

Gibson et al., The capsular polysaccharide complex of *Bacteroides fragilis* induces cytokine production from human and murine phagocytic cells. Infect Immun. Mar. 1996;64(3):1065-9.

Glazebrook et al., A novel exopolysaccharide can function in place of the calcofluor-binding exopolysaccharide in nodulation of alfalfa by *Rhizobium meliloti*. Cell. Feb. 24, 1989;56(4):661-72.

Golgher et al., Galactofuranose-containing glycoconjugates of epimastigote and trypomastigote forms of Trypanosoma cruzi. Mol Biochem Parasitol. Aug. 1993;60(2):249-64.

Gonzalez-Hernandez et al., Peripheral blood CD161+ T cells from asthmatic patients are activated during asthma attack and predominantly produce IFN-gamma. Scand J Immunol. Apr. 2007;65(4):368-75.

Groux et al., a CD4+ T-cell subset inhibits antigen-specific T-cell responses and prevents colitis. Nature. Oct. 16, 1997;389(6652):737-42.

Groux et al., Type 1 T-regulatory cells: their role in the control of immune responses. Transplantation. May 15, 2003;75(9 Suppl):8S-12S.

Hafler et al., Anti-CD4 and anti-CD2 monoclonal antibody infusions in subjects with multiple sclerosis. Immunosuppressive effects and human anti-mouse responses. J Immunol. Jul. 1, 1988;141(1):131-8.

Hamelmann et al., Noninvasive measurement of airway responsiveness in allergic mice using barometric plethysmography. Am J Respir Crit Care Med. Sep. 1997;156(3 Pt 1):766-75.

Haregewoin et al., Human gamma delta+ T cells respond to mycobacterial heat-shock protein.Nature. Jul. 27, 1989;340(6231):309-12.

Hertl et al., T cell control in autoimmune bullous skin disorders. J Clin Invest. May 2006;116(5):1159-66. Review.

Hirata et al., Cytokine synthesis of human monocytes stimulated by triple or single helical conformer of an antitumour (1—>3)-beta-D-glucan preparation, sonifilan. Zentralbl Bakteriol. Nov. 1998;288(3):403-13.

Hutloff et al., ICOS is an inducible T-cell co-stimulator structurally and functionally related to CD28. Nature. Jan. 21, 1999;397(6716):263-6.

Itokazu et al., Abscess formation as a complication caused by post-operative osteomyelitis of the femur. Arch Orthop Trauma Surg. 1998;118(1-2):99-102. Review.

Jennings et al., Induction of meningococcal group B polysaccharide-specific IgG antibodies in mice by using an N-propionylated B polysaccharide-tetanus toxoid conjugate vaccine. J Immunol. Sep. 1, 1986;137(5):1708-13.

Jennings et al., Immunochemistry of groups A, B, and C meningococcal polysaccharide-tetanus toxoid conjugates. J Immunol. Sep. 1981;127(3):1011-8.

Jennings et al., Structure of the complex polysaccharide C-substance from *Streptococcus pneumoniae* type 1. Biochemistry. Sep. 30, 1980;19(20):4712-9.

Jonuleit et al., Identification and functional characterization of human CD4(+)CD25(+) T cells with regulatory properties isolated from peripheral blood. J Exp Med. Jun. 4, 2001;193(11):1285-94.

Jonuleit et al., The regulatory T cell family: distinct subsets and their interrelations. J Immunol. Dec. 15, 2003;171(12):6323-7. Review.

Jotwani et al., Pathogenicity of *Bacteroides fragilis* group in rat intra-abdominal abscesses. Microbiol Immunol. 1992;36(10):1041-9.

Kalka-Moll et al., *Bacteriodes fragilis* NCTC 9343 Capsular Polysaccharide PS A and the Effect of Chain Length of T cell Proliferation. Abstracts of the 98*th* Gen Mtg of the American Soc for Microbiol. 1998;98:123. Abstract B-405.

Kalka-Moll et al., Effect of molecular size on the ability of zwitterionic polysaccharides to stimulate cellular immunity. J Immunol. Jan. 15, 2000;164(2):719-24.

Kalka-Moll et al., Immunochemical and biological characterization of three capsular polysaccharides from a single *Bacteroides fragilis* strain. Infect Immun. Apr. 2001;69(4):2339-44.

Kasper et al., Protective efficacy of immunization with capsular antigen against experimental infection with *Bacteroides fragilis*. J Infect Dis. Nov. 1979;140(5):724-31.

Kasper et al., Capsular polysaccharides and lipopolysaccharides from two *Bacteroides fragilis* reference strains: chemical and immunochemical characterization. J Bacteriol. Feb. 1983;153(2):991-7.

Kasper et al., Surface antigens as virulence factors in infection with *Bacteroides fragilis*. Rev Infect Dis. Mar.-Apr. 1979;1(2):278-90.

Kasper et al., The polysaccharide capsule of *Bacteroides fragilis* subspecies fragilis: immunochemical and morphologic definition. J Infect Dis. Jan. 1976;133(1):79-87.

Kato et al., Interleukin 10 reduces mortality from severe peritonitis in mice. Antimicrob Agents Chemother. Jun. 1995;39(6):1336-40.

Kenne et al., Structural studies of the O-specific side-chains of the *Shigella sonnei* phase I lipopolysaccharide. Carbohydrate Res. 1980;78:119-126.

Kennedy et al., Prevention of experimental postoperative peritoneal adhesions by N,O-carboxymethyl chitosan. Surgery. Nov. 1996;120(5):866-70.

Knetsch et al., Polymers with tunable toxicity: a reference scale for cytotoxicity testing of biomaterial surfaces. J Biomed Mater Res A. Sep. 15, 2007;82(4):947-57.

Knirel et al., Somatic antigens of *Pseudomonas aeruginosa*. The structure of O-specific polysaccharide chains of lipopolysaccharides of *P. aeruginosa* O3 (Lányi), O25 (Wokatsch) and Fisher immunotypes 3 and 7. Eur J Biochem. Sep. 15, 1987;167(3):549-61.

Knirel et al., The structure of O-specific polysaccharides and serological classification of *Pseudomonas aeruginosa* (a review). Acta Microbiol Hung. 1988;35(1):3-24. Review.

Krause et al., An inhibitor of cell proliferation associated with adhesion formation is suppressed by N,O-carboxymethyl chitosan. J Invest Surg. Mar.-Apr. 1998;11(2):105-13.

Kulicke et al., Correlation between immunological activity, molar mass, and molecular structure of different (1—>3)-beta-D-glucans. Carbohydr Res. Jan. 2, 1997;297(2):135-43.

Kurup et al., Antibody response to low-molecular-weight antigens of *Aspergillus fumigatus* in allergic bronchopulmonary aspergillosis. J Clin Microbiol. Jun. 1989;27(6):1312-6.

Lindberg et al., Virulence factors in infections with *Bacteroides fragilis*: isolation and characterization of capsular polysaccharide and lipopolysaccharide. Scand J Infect Dis Suppl. 1982;35:45-52.

Lindberg et al., Structural studies of the capsular polysaccharide from *Streptococcus pneumoniae* type 1. Carbohydr Res. Jan. 1, 1980;78(1):111-7.

Maconi et al., Contrast radiology, computed tomogrpahy, and ultrasonography in detecting internal fistulas and intra-abdominal abscesses in Chrohn's disease: a prospective comparative study. Amer J Gast. 2003;98(7):1545-1555.

Mäkelä et al., IL-10 is necessary for the expression of airway hyper-responsiveness but not pulmonary inflammation after allergic sensitization. Proc Natl Acad Sci U S A. May 23, 2000;97(11):6007-12.

Mamessier et al., Cytokines in atopic diseases: revisiting the Th2 dogma. Eur J Dermatol. Mar.-Apr. 2006;16(2):103-13. Review.

Mazmanain et al., The love-hate relationship between bacterial polysaccharides and the host immune system. Nature Reviews Immunology 6, 849 (2006).

Meisel-Mikolajczyk et al., Human T cell adhesion to endothelium stimulated by membrane components extracted from strains of *Bacteroides vulgatus* (member of B. fragilis group). Arch Immunol Ther Exp (Warsz). 1993;41(2):129-31.

Mojtabavi et al., Long-lived Th2 memory in experimental allergic asthma. J Immunol. Nov. 1, 2002;169(9):4788-96.

Montz et al., Interleukin 10: ability to minimize postoperative intraperitoneal adhesion formation in a murine model. Fertil Steril. Jun. 1994;61(6):1136-40.

Moore, The List Goes on, New Additions to the Autoimmune Disease Roster. http://autoimmunedisease.suite101.com/blog.cfm/the_list_goes_on. pp. 1-3.

Mulholland et al., Strategies for the control of *pneumococcal* diseases. Vaccine. Jul. 30, 1999;17 Suppl 1:S79-84. Review.

Nielsen et al., Applications of peptide nucleic acids. Curr Opin Biotechnol. Feb. 1999;10(1):71-5. Review.

Oh et al., CD4 T-helper cells engineered to produce IL-10 prevent allergen-induced airway hyperreactivity and inflammation. J Allergy Clin Immunol. Sep. 2002;110(3):460-8.

Ohno et al., Enhancement of LPS triggered TNF-alpha (tumor necrosis factor-alpha) production by (1—>3)-beta-D-glucans in mice. Biol Pharm Bull. Jan. 1995;18(1):126-33.

Ohno et al., Comparison of the immunopharmacological activities of triple and single-helical schizophyllan in mice. Biol Pharm Bull. Sep. 1995;18(9):1242-7.

Onderdonk et al., Evidence for T cell-dependent immunity to *Bacteroides fragilis* in an intraabdominal abscess model. J Clin Invest. Jan. 1982;69(1):9-16.

Onderdonk et al., The capsular polysaccharide of *Bacteroides fragilis* as a virulence factor: comparison of the pathogenic potential of encapsulated and unencapsulated strains. J Infect Dis. Jul. 1977;136(1):82-9.

Pantosti et al., *Bacteroides fragilis* strains express multiple capsular polysaccharides. J Clin Microbiol. Jul. 1993;31(7):1850-5.

Pantosti et al., Immunochemical characterization of two surface polysaccharides of *Bacteroides fragilis*. Infect Immun. Jun. 1991;59(6):2075-82.

Paoletti et al., Effects of chain length on the immunogenicity in rabbits of group *B Streptococcus* type III oligosaccharide-tetanus toxoid conjugates. J Clin Invest. Jan. 1992;89(1):203-9.

Pavliak et al., Structural elucidation of the capsular polysaccharide of *Bacteroides fragilis* strain 23745M1. Carbohydr Res. Oct. 2, 1995;275(2):333-41.

Perumal et al., Protective effect of interleukin-2 on experimental intra-abdominal abscess development due to *Bacteriodes fragilis*. Clinical Research. 1990;38(2):550A.

Ranua et al., Serum IgA, IgG, and IgM concentrations in patients with epilepsy and matched controls: a cohort-based cross-sectional study. Epilepsy Behav. Mar. 2005;6(2):191-5.

Reed et al., A simple method of estimating fifty percent endpoints. Am J Hyg. 1938;27:493-497.

Riesenfeld et al., Biosynthesis of heparin. Assay and properties of the microsomal N-acetyl-D-glucosaminyl N-deacetylase.J Biol Chem. Feb. 10, 1980;255(3):922-8.

Roncarolo et al., Type 1 T regulatory cells. Immunol Rev. Aug. 2001;182:68-79. Review.

Rypens et al., Percutaneous drainage of abdominal abscesses in pediatric Crohn's disease. AJR Am J Roentgenol. Feb. 2007;188(2):579-85.

Schlegel et al., A synthetic random basic copolymer with promiscuous binding to class II major histocompatibility complex molecules inhibits T-cell proliferative responses to major and minor histocompatibility antigens in vitro and confers the capacity to prevent murine graft-versus-host disease in vivo. Proc Natl Acad Sci U S A. May 1996 14;93(10):5061-6. Erratum in: Proc Natl Acad Sci U S A Aug. 6, 1996;93(16):8796.

Schneider et al., De novo design of molecular architectures by evolutionary assembly of drug-derived building blocks. J Comput Aided Mol Des. Jul. 2000;14(5):487-94.

Segal et al., Severe insulin resistance secondary to insulin antibodies: successful treatment with the immunosuppressant MMF. Pediatr Diabetes. Jun. 2008;9(3 Pt 1):250-4.

Sellin et al., Conformational analysis of a toxic peptide from Trimeresurus wagleri which blocks the nicotinic acetylcholine receptor. Biophys J. Jan. 1996;70(1):3-13.

Shapiro et al., Cellular control of abscess formation: role of T cells in the regulation of abscesses formed in response to Bacteroides fragilis. J Immunol. Jul. 1, 1986;137(1):341-6.

Shapiro et al., Cellular immunity to Bacteroides fragilis capsular polysaccharide. J Exp Med. Apr. 1, 1982;155(4):1188-97.

Sharpe et al., The B7-CD28 superfamily. Nat Rev Immunol. Feb. 2002;2(2):116-26. Review.

Shevach et al., CD4+ CD25+ suppressor T cells: more questions than answers. Nat Rev Immunol. Jun. 2002;2(6):389-400. Review.

Simmons et al., Synthesis and membrane permeability of PNA-peptide conjugates. Bioorg Med Chem Lett. 1997;7(23):3001-6.

Stein, Thymus-independent and thymus-dependent responses to polysaccharide antigens. J Infect Dis. Jun. 1992;165 Suppl 1:S49-52. Review.

Suri-Payer et al., CD4+CD25+ T cells inhibit both the induction and effector function of autoreactive T cells and represent a unique lineage of immunoregulatory cells. J Immunol. Feb. 1, 1998;160(3):1212-8.

Szu et al., Relation between structure and immunologic properties of the Vi capsular polysaccharide. Infect Immun. Dec. 1991;59(12):4555-61.

Tang et al., Th type 1-stimulating activity of lung macrophages inhibits Th2-mediated allergic airway inflammation by an IFN-gamma-dependent mechanism. J Immunol. Feb. 1, 2001;166(3):1471-81.

Taylor et al., Stoichiometric depolymerization of polyuronides and glycosaminoglycuronans to monosaccharides following reduction of their carbodiimide-activated carboxyl groups. Biochemistry. Apr. 11, 1972;11(8):1383-8.

Teitelbaum et al., Immunomodulation of experimental autoimmune encephalomyelitis by oral administration of copolymer 1. Proc Natl Acad Sci U S A. Mar. 30, 1999;96(7):3842-7.

Teitelbaum et al., Specific inhibition of the T-cell response to myelin basic protein by the synthetic copolymer Cop 1. Proc Natl Acad Sci U S A. Dec. 1988;85(24):9724-8.

Teitelbaum et al., Synthetic copolymer 1 inhibits human T-cell lines specific for myelin basic protein. Proc Natl Acad Sci U S A. Jan. 1, 1992;89(1):137-41.

Teitelbaum et al., Unprimed spleen cell populations recognize macrophage-bound antigen with opposite net electric charge. Proc Natl Acad Sci U S A. Apr. 1977;74(4):1693-6.

Thomas et al., Randomized controlled trial of short bursts of a potent topical corticosteroid versus prolonged use of a mild preparation for children with mild or moderate atopic eczema. BMJ. 2002;324:1-7.

Tournoy et al., Endogenous interleukin-10 suppresses allergen-induced airway inflammation and nonspecific airway responsiveness. Clin Exp Allergy. Jun. 2000;30(6):775-83.

Tzianabos et al., Structural basis for polysaccharide-mediated protection against intraabdominal abscess forination. 94th ASM General Meeting. May 23-27, 1994. Las Vegas, Nevada. Abstract B-206:65.

Tzianabos et al., Bacterial structure and functional relation to abscess formation. Infect Agents Dis. Oct. 1994;3(5):256-65. Review.

Tzianabos et al., Effect of surgical adhesion reduction devices on the propagation of experimental intra-abdominal infection. Arch Surg. Nov. 1999;134(11):1254-9.

Tzianabos et al., IL-2 mediates protection against abscess formation in an experimental model of sepsis. J Immunol. Jul. 15, 1999;163(2):893-7.

Tzianabos et al., Polysaccharide-mediated protection against abscess formation in experimental intra-abdominal sepsis. J Clin Invest. Dec. 1995;96(6):2727-31.

Tzianabos et al., Protection against experimental intraabdominal sepsis by two polysaccharide immunomodulators. J Infect Dis. Jul. 1998;178(1):200-6.

Tzianabos et al., Structural characteristics of polysaccharides that induce protection against intra-abdominal abscess formation. Infect Immun. Nov. 1994;62(11):4881-6.

Tzianabos et al., Structural features of polysaccharides that induce intra-abdominal abscesses. Science. Oct. 15, 1993;262(5132):416-9.

Tzianabos et al., Structural rationale for the modulation of abscess formation by Staphylococcus aureus capsular polysaccharides. Proc Natl Acad Sci U S A. Jul. 31, 2001;98(16):9365-70. Epub Jul. 24, 2001.

Tzianabos et al., Structure and function of Bacteroides fragilis capsular polysaccharides: relationship to induction and prevention of abscesses. Clin Infect Dis. Jun. 1995;20 Suppl 2:S132-40. Review.

Tzianabos et al., Structure-function relationships for polysaccharide-induced intra-abdominal abscesses. Infect Immun. Aug. 1994;62(8):3590-3.

Tzianabos et al., T cells activated by zwitterionic molecules prevent abscesses induced by pathogenic bacteria. J Biol Chem. Mar. 10, 2000;275(10):6733-40.

Tzianabos et. al., T Cell Activation by Zwitterionic polysaccharides and peptide mimetics prevents antrabdominal abscess formation. Abstracts of the 99th General Meeting of the American Society for Microbiology. Chicago, US: May 30-Jun. 3, 1999. Jun. 28, 1999;99:37-38.

Tzianabos et al., The capsular polysaccharide of Bacteroides fragilis comprises two ionically linked polysaccharides. J Biol Chem. Sep. 5, 1992;267(25):18230-5.

Tzianabos et al., Characteristics of bacterial polysaccharides that activate T cells. The International Carbohydrate Symposium XVII. Jul. 21, 1994.

Van Scott et al., IL-10 reduces Th2 cytokine production and eosinophilia but augments airway reactivity in allergic mice. Am J Physiol Lung Cell Mol Physiol. Apr. 2000;278(4):L667-74.

Vann et al., The structure of the capsular polysaccharide (K5 antigen) of urinary-tract-infective Escherichia coli 010:K5:H4. A polymer similar to desulfo-heparin. Eur J Biochem. May 15, 1981;116(2):359-64.

Viret et al., Molecular cloning and characterization of the genetic determinants that express the complete Shigella serotype D (Shigella sonnei) lipopolysaccharide in heterologous live attenuated vaccine strains. Mol Microbiol. Jan. 1993;7(2):239-52.

Wang et al., Structural basis of the abscess-modulating polysaccharide A2 from Bacteroides fragilis. Proc Natl Acad Sci U S A. Dec. 5, 2000;97(25):13478-83.

Wang et al., Structure characterization of an abscessogenic capsular polysaccharide from Bacteriodes fragilis by NMR spectroscopy. XIX International Conference of NMR in Biological Systems. Florence, Italy. Aug. 20-25, 2000. Abstract.

Wehr et al., Anti-low-density lipoprotein antibodies in alcoholics without and with liver disease and in social drinkers. Alcohol Alcohol. Jan.-Feb. 1997;32(1):43-9.

Wessels et al., Structure and immunochemistry of an oligosaccharide repeating unit of the capsular polysaccharide of type III group B Streptococcus. A revised structure for the type III group B Streptococcal polysaccharide antigen. J Biol Chem. Jun. 15, 1987;262(17):8262-7.

Wujek et al., A carbohydrate polymer that effectively prevents epidural fibrosis at laminectomy sites in the rat. Exp Neurol. Nov. 1991;114(2):237-45.

Yokoyama et al., Adhesion behavior of rat lymphocytes to poly(ether)-poly(amino acid) block and graft copolymers. J Biomed Mater Res. Sep. 1986;20(7):867-78.

Yoshii, Cytotoxic effects of acrylates and methacrylates: relationships of monomer structures and cytotoxicity. J Biomed Mater Res. Dec. 15, 1997;37(4):517-24.

Zaleznik et al., A soluble suppressor T cell factor protects against experimental intraabdominal abscesses. J Clin Invest. Mar. 1985;75(3):1023-7.

Zhu et al., Oral administration of type-II collagen peptide 250-270 suppresses specific cellular and humoral immune response in collagen-induced arthritis. Clin Immunol. Jan. 2007;122(1):75-84. Epub Oct. 11, 2006.

Bilo, B.M., et al.; "Diagnosis of Hymenoptera venom allergy"; Allergy 2005; 60:1339-1349.

Boguniewicz, M.; "The autoimmune nature of chronic urticaria"; Allergy Asthma Proc 2008; 29:433-438.

Gelu-Simeon, et al.; "Evaluation and predictive factors of thyroid disorder due to interferon alpha in the treatment of hepatitis C"; World J Gastroenterol 2009; 15(3):328-333.

Greenberger, P.A.; "Drug allergy"; J Allergy Clin Immunol 2006; 117(2):S464-S470.

Jyonouchi, H.; "Non-IgE Mediated Food Allergy"; Inflammation & Allergy—Drug Targets 2008; 7(3):1-8.

Kormelink, T.G., et al.; "Atopic and non-atopic allergic disorders: current insights into the possible involvement of free immunoglobulin light chains"; Clinical and Experimental Allergy 2008; 39:33-42.

Miller et al.; "Severe asthma and the omalizumab option"; Clinical and Molecular Allergy 2008; 6(4):1-13.

Norman; "Thyroiditis—Inflammation of the thyroid gland"; Endocrineweb 2009; www.endocrineweb.com/throiditis.html, 1-4. Downloaded Jul. 28, 2009.

Poonawalla, T., et al.; "Urticaria a Review"; Am J Clin Dermotol 2009; 10(1):9-21.

Shaklee and Conrad; "Hydrazinolysis of heparin and other glycosaminoglycans"; Biochem. J. (1984); 217: 187-197.

\* cited by examiner

ZWITTERIONIC POLYSACCHARIDES FOR PROMOTION OF IMMUNE SYSTEM MATURATION AND HEALTH

RELATED APPLICATIONS

This application is a national stage filing under 35 U.S.C. §371 of international application PCT/US2007/003160, filed Feb. 5, 2007, which claims the benefit under 35 U.S.C. §119 (e) from U.S. provisional application Ser. No. 60/765,800, filed Feb. 6, 2006, the entire contents of each of which are herein incorporated by reference.

BACKGROUND OF THE INVENTION

Immediately after a sterile birth, mammals are initiated into an organized and life-long process of colonization by foreign organisms. Shaped by eons of evolution, some host-bacterial associations have developed into prosperous relationships creating diverse environments. No better example exists in biology than the astounding numbers of bacteria harbored by the lower gastrointestinal tract of mammals (Hooper et al., 1998). By young adulthood, humans and other mammals are host to ~$10^{12}$ viable bacteria per gram of colonic content, consisting of 500-1000 microbial species and outnumbering host cells by 100-fold (Hooper and Gordon, 2001). The magnitude of this interaction between commensal bacteria and mammals must predictably exert fundamental influences on the physiology of both. The most impressive feature of this relationship may be that the host not only tolerates but has evolved to require colonization by commensal microorganisms for its own development and health.

Autochthonous (indigenous) bacteria in the mammalian gut have long been appreciated for potential benefits to the host: provision of essential nutrients, metabolism of indigestible compounds, defense against colonization by opportunistic pathogens, and contributions to the development of the intestinal architecture (Hooper et al., 2000; Hooper et al., 2002). For some years workers have sought to understand how and why the immunocompetent gut environment allows the presence of multitudinous foreign organisms. Researchers have proposed that certain commensal bacteria have evolved to aid in the host's health; several organisms are being studied for probiotic (beneficial) potential (Guarner and Malagelada, 2003; Rastall, 2004). The "hygiene hypothesis" suggests that the appropriate bacterial constitution of the human microflora is a factor in protection from allergy and asthma (Umetsu et al, 2002; Von Hertzen and Haahtela, 2004). Investigations have shown that the interactions of commensal bacteria with Toll-like receptors are critical for intestinal homeostasis (Rakoff-Nahoum et al., 2004). The intimate relationships between commensal microorganisms and the host immune system are increasingly evident (Macpherson and Harris, 2004; Noverr and Huffnagle, 2004).

The mammalian immune system is a dynamic and remarkable organ. In recognizing, responding, and adapting to countless foreign and self molecules, the immune system is central to processes of health and disease. CD4$^+$ T cells, a major component of the immune system, are required for vital aspects of proper immune function, from reactions to infectious agents to control of autoimmune reactions and cancers (Janeway et al., 2001). Effector CD4$^+$ T cells are of two general subtypes: T helper 1 ($T_H1$) and T helper 2 ($T_H2$), each carrying out distinct and opposing activities. The proper balance between $T_H1$ and $T_H2$ immunologic responses is critical to overall human and animal health (Neurath et al., 2002; Sheikh and Strachan, 2004). A role for commensal bacteria in establishing this equilibrium has been postulated (Bowman and Holt, 2001; Rook and Brunet, 2002).

*Bacteroides fragilis* (*B. fragilis*) is a ubiquitous and important gram-negative anaerobe that colonizes the mammalian lower gastrointestinal tract. *Bacteroides* spp. are among the earliest-colonizing and most numerically prominent constituents of the gut microflora (Kononen et al., 1992). Although capsular polysaccharides are common in many bacterial species, *B. fragilis* elaborates an unprecedented eight distinct surface polysaccharides (Krinos et al., 2001). Several of these polysaccharides have a characteristic zwitterionic structure, with both positive and negative charges in each repeating unit (Tzianabos et al., 1993).

Zwitterionic polysaccharides (ZPSs) are unique T cell-dependent antigens that specifically mediate the proliferation of CD4$^+$ T cells in vitro (Brubaker et al., 1999; Tzianabos and Kasper, 2002). Adoptive transfer experiments have shown that responses to polysaccharide A (PSA), the most immunodominant ZPS of *B. fragilis*, are conferred by CD4$^+$ T cells, not by B cells or other T cells (Tzianabos et al., 1999). PSA is internalized and processed within endosomes of antigen-presenting cells (APCs) (Cobb et al., 2004). Subsequent presentation of processed polysaccharide by major histocompatibility complex class II (MHC II) molecules activates CD4$^+$ T cells and represents a previously undescribed pathway of antigen presentation. Thus ZPSs appear to have evolved novel biological activities shaped by co-evolution with the host immune system.

SUMMARY OF THE INVENTION

The invention is based in part on the discovery by the applicants that enteral administration of a zwitterionic polysaccharide, such as the bacterial capsular polysaccharide PSA isolated from *B. fragilis*, can influence overall immune homeostasis through the zwitterionic polysaccharide's ability to mediate establishment of a proper $T_H1/T_H2$ balance for the host, a fundamental aspect of healthy immunologic function. More particularly, according to the invention ZPSs can be included in nutritional formulas and nutritional supplements and administered to a subject to help promote and maintain a desirable balance between $T_H1$ and $T_H2$ throughout the immune system. Establishment of a proper $T_H1/T_H2$ balance using the compositions and methods of the invention promotes a state of health characterized by diminished risk of having or developing a number of immune-mediated conditions associated with a default $T_H2$ phenotype, e.g., atopy (allergy predisposition), allergic asthma, and autoimmunity. Compositions and methods of the invention are thus useful whenever it is desirable to provide a $T_H1$ stimulus to the immune system of a mammalian subject. In particular, the compositions and methods of the invention are useful in stimulating a proper $T_H1/T_H2$ balance in human infants and other human subjects that have an immature immune system or predisposition to develop a default $T_H2$ phenotype.

In one aspect the invention is a nutritional formula or nutritional supplement composition, comprising an isolated zwitterionic polysaccharide consisting essentially of repeating units, wherein each repeating unit comprises two to ten monosaccharides and a positively charged free amino moiety and a negatively charged moiety selected from the group consisting of carboxylate, phosphate, phosphonate, sulfate, and sulfonate.

In one aspect the invention is a method for preparing a nutritional formula or nutritional supplement composition. The method according to this aspect of the invention includes the step of combining an isolated zwitterionic polysaccharide, said polysaccharide consisting essentially of repeating units, wherein each repeating unit comprises two to ten monosaccharides and a positively charged free amino moiety and a negatively charged moiety selected from the group consisting of carboxylate, phosphate, phosphonate, sulfate, and sulfonate, with a nutritional formula or nutritional supplement that is otherwise free of the isolated zwitterionic polysaccharide.

In one aspect the invention is a method of promoting immune system maturation in an infant. The method according to this aspect of the invention includes the step of enterally administering to the infant an effective amount of a nutritional formula or nutritional supplement composition, said composition comprising an isolated zwitterionic polysaccharide consisting essentially of repeating units, wherein each repeating unit comprises two to ten monosaccharides and a positively charged free amino moiety and a negatively charged moiety selected from the group consisting of carboxylate, phosphate, phosphonate, sulfate, and sulfonate.

In one embodiment the zwitterionic polysaccharide is a naturally occurring bacterial capsular polysaccharide.

In one embodiment the zwitterionic polysaccharide is a *B. fragilis* capsular polysaccharide A (PSA). In one embodiment the PSA is PSA1.

In one embodiment the PSA is PSA2.

In one embodiment the zwitterionic polysaccharide is a *B. fragilis* capsular polysaccharide B (PSB).

In one embodiment the zwitterionic polysaccharide is selected from the group consisting of *Shigella sonnet* Phase I lipopolysaccharide O-antigen, *Streptococcus pneumoniae* type 1 capsular polysaccharide, and *Streptococcus pneumoniae* group antigen C substance.

In one embodiment the nutritional formula or nutritional supplement is a nutritional formula.

In one embodiment the nutritional formula or nutritional supplement is a nutritional supplement.

In one embodiment the enterally administering is orally administering.

In one embodiment the infant is 0-6 months old.

In one embodiment the immune system maturation is an increase in a T helper 1 marker to a T helper 2 marker.

In one embodiment the T helper 1 marker is a cytokine selected from interferon gamma (IFN-γ) and interleukin 2 (IL-2).

In one embodiment the T helper 2 marker is a cytokine selected from interleukin 4 (IL-4) and interleukin 5 (IL-5).

Figure 1A:
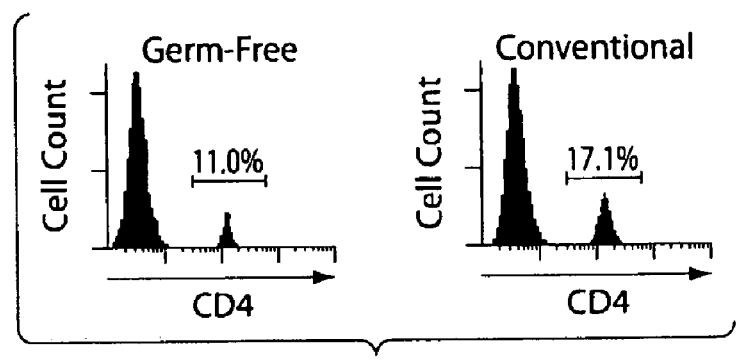
FIG. 1. Cellular and Physical Immune Maturation in Germ-Free Mice Requires PSA Production During Intestinal *B. fragilis* Colonization.

(A) Flow cytometry (FC) analysis of anti-CD4-stained splenic lymphocytes from conventionally colonized (CNV) and germ-free (GF) mice reveals depletion of $CD4^+$ T cells in the absence of colonizing microflora in the gastrointestinal (GI) tract. Results are representative of 4 experiments with pools of 3-5 mice.

(B) Quantitation of fecal colony forming units (CFU) during mono-colonization of GF mice with wild-type *B. fragilis* or an isogenic mutant deficient in PSA production (*B. fragilis* ΔPSA) reveals equivalent counts of viable bacteria from fecal pellets. Inset: Immunoblot of bacterial extracts with anti-PSA after SDS-PAGE separation and electro-transfer to PVDF membranes shows the lack of PSA expression by *B. fragilis* ΔPSA.

(C) FC of anti-CD4-stained splenic lymphocytes from GF mice shows that intestinal mono-colonization of mice with *B. fragilis* results in complementation of $CD4^+$ T cells. In the presence of every other antigen produced during colonization with *B. fragilis* ΔPSA, the absence of PSA results in no increase in $CD4^+$ T cell counts. Results are representative of >10 experiments with single or pools of 3-5 mice.

(D) FC of splenic lymphocytes from CNV and GF mice colonized with wild-type or *B. fragilis* ΔPSA reveals no significant differences in CD19+ B cells (upper panels) or $CD8^+$ T cells (lower panels) in the $CD4^-$ fraction. Results are representative of 4 experiments with pools of 3-5 mice.

(E) Hematoxylin and eosin (H&E) stained sections of spleens from CNV mice (right), GF mice mono-colonized with wild-type *B. fragilis* (left) and with *B. fragilis* ΔPSA (center). White pulp containing lymphocytes appears as darker-staining follicular structures (arrows). The lack of large, well-defined follicles in mice colonized with *B. fragilis* ΔPSA is a measure of T cell depletion and reflects developmental defects in organogenesis. All images were taken at the same magnification.

FIG. 2. Purified PSA Treatment Is Sufficient for Expansion of $CD4^+$ T Cells.

(A) FC of anti-CD4-stained splenic lymphocytes from GF mice treated intraperitoneally with PSA or phosphate buffered saline (PBS) reveals PSA-dependent restoration of $CD4^+$ T cells. Results are representative of 2 experiments with pools of 4 mice.

(B) FC shows that oral treatment of conventional C57BL/6 and BALB/c mice with purified PSA (PSA) results in an increase in $CD4^+$ T cell proportion among splenic lymphocytes over controls (PBS). Results are representative of 4 experiments with pools of 3-5 mice.

(C) FC shows that oral treatment of conventional mice with purified PSA does not affect proportions of $CD8^+$ T cells or $CD19^+$ B cells among the $CD4^-$ splenic lymphocyte population.

FIG. 3. PSA Is Specifically Recognized by Dendritic Cells (DCs) in the GI Tract and in Vitro, with Consequent Cell Activation.

(A) Oral treatment of mice with Alexa-594-labeled PSA results in antigen uptake by $CD11c^+$ DCs from mesenteric lymph nodes (MLNs). FC of $CD11c^+$ gated cells (boxed left panel, middle) analyzed for the presence of PSA (horizontal axis of right panels) shows co-localization of PSA with DCs. FC of isolated MLNs reveals no PSA associated with $CD4^+$ T cells from the same lymph nodes (boxed left panel, bottom). Isotype control is shown in the top left panel. Shaded histograms represent unstained control, and thick black lines denote Alexa-594 signal from PSA on the horizontal axis. No PSA is detectable in splenic tissues (data not shown).

(B) Confocal microscopy of anti-CD11c-labeled (originally green) and 24-hour PSA-treated (originally red) bone marrow-derived dendritic cells (BMDCs) in culture illustrate antigen in endosomes and surface display (arrowheads). Central image is the XY-plane of a medial Z-section, upper and side panels are assembled Z-stacks.

(C) FC of BMDCs cultured for 24 hours with PSA shows activation by up-regulation of MHC II (horizontal axis) among $CD11c^+$ cells (vertical axis).

(D) FC of $CD11c^+$ BMDCs cultured for 24 hours with PSA shows activation through up-regulation of the co-stimulatory molecule CD86 (B7.2).

FIG. 4. PSA Induces CD4+ T Cell Proliferation and $T_H1$ Cytokine Production in Vitro.

(A) CD4+ T-cell proliferation by [$^3$H]thymidine incorporation increases in response to irradiated BMDCs ($1\times10^6$) incubated with PSA. Treatment of co-cultures with NAc-PSA results in no increase in cell proliferation. Lipopolysaccharide (LPS) treatment or DCs or T cells alone do not support CD4+ T-cell proliferation. Results are representative of 3 experiments.

(B) PSA treatment stimulates IFN-γ in DC-T cell co-cultures, as measured by enzyme-linked immunosorbent assay (ELISA) of culture supernatants after 48 hours of treatment. NAc-PSA treatment has no effect. Treatment with anti-CD3, LPS, and staphylococcal enterotoxin A (SEA), all known stimulators of $T_H1$ cytokine expression, results in IFN-γ production. DCs or T cells alone treated with PSA do not support cytokine expression.

(C) PSA treatment does not stimulate expression of IL-4 in DC-T cell co-cultures. Treatment with anti-CD3 and SEA, known stimulators of $T_H2$ cytokine expression, results in IL-4 production.

FIG. 5. PSA Signals Through the IL-12/Stat4 Pathway to Mediate $T_H1$ Cytokine Production, Which Requires Presentation by MHC II.

(A) PSA stimulates expression of IL-12, the $T_H1$ determining signal, in DC-T cell co-cultures ($1\times10^6$ of each cell type). NAc-PSA treatment has no effect. Anti-CD3 and SEA serve as controls for IL-12 expression by BMDCs. Results are representative of 2 experiments.

(B) IL-12 is required for PSA-mediated IFN-γ production. IFN-γ expression is abolished in DC-T cell co-cultures treated with PSA (100 μg/mL) in the presence neutralizing antibody to IL-12. Neutralization of IL-12 does not inhibit anti-CD3-mediated IFN-γ expression, which is IL-12 independent.

Figure 4A:
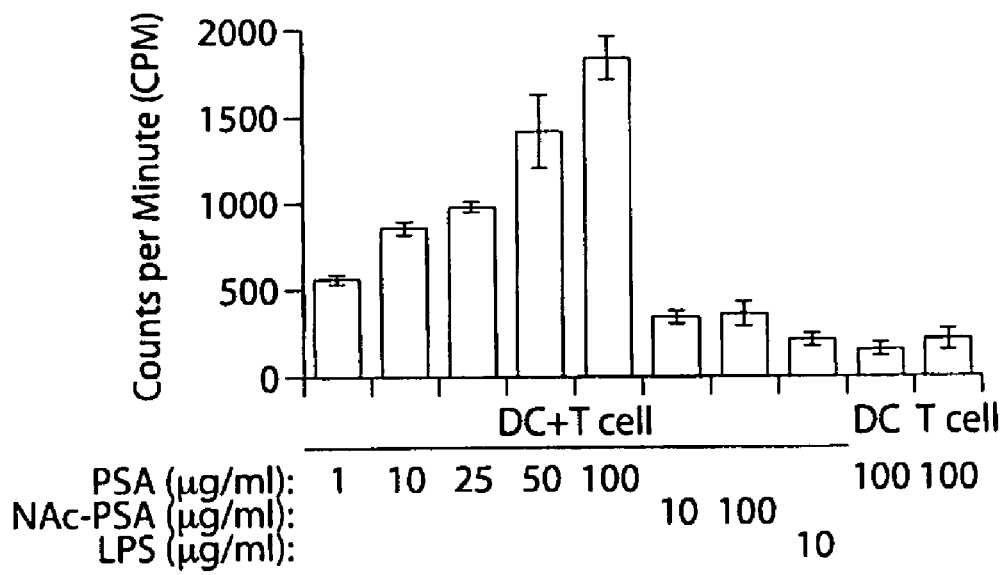
Figure 4B:
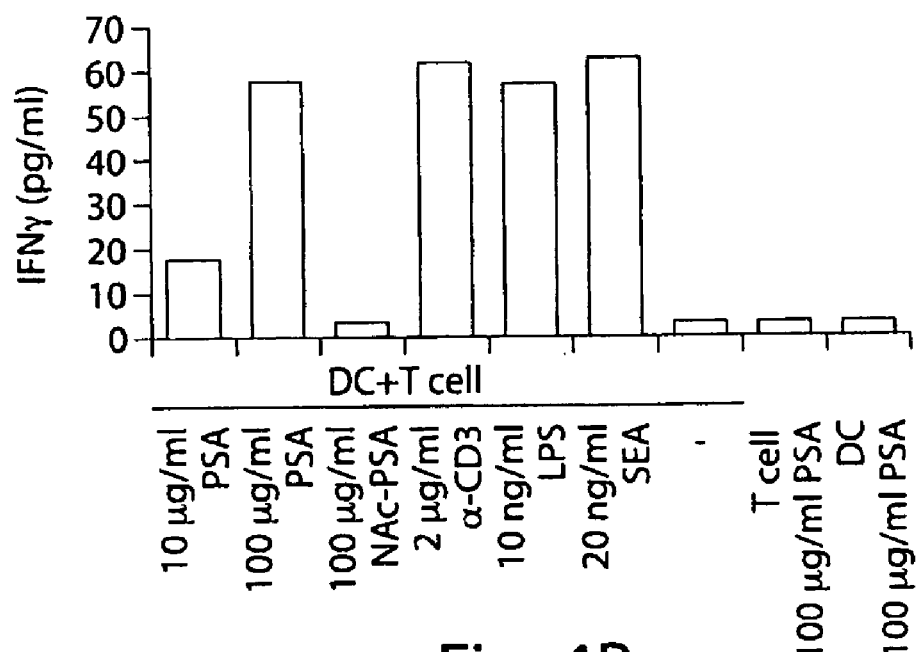

(C) PSA signals through Stat4 to induce IFN-γ secretion by T cells. IFN-γ expression from DC-T cell co-cultures treated with PSA (100 μg/mL) is reduced when CD4+ T cells are purified from spleens of stat4 knockout rather than wild-type mice (FIG. 4B).

(D) MHC class II expressed on DCs is necessary for PSA-mediated IFN-γ expression by CD4 T cells. IFN-γ production by DC-T cell co-cultures treated with PSA (100 μg/mL) is reduced when BMDCs are from MHC II knockout mice. NAc-PSA (100 μg/mL) treatment of wild-type DCs (MHC II$^{+/+}$) serves as the control for PSA-specific IFN-γ expression.

FIG. 6. Colonization of GF Mice with PSA-Producing *B. fragilis* Corrects $T_H1/T_H2$ Imbalances Associated with Cytokine-Mediated Pathologies.

(A) IL-4 production from splenic CD4+ T cells stimulated in vitro with anti-CD3/anti-CD28 (2 μg/mL each), reveals that PSA is required to correct the $T_H2$ skew in GF mice. Compared with CNV mice, OF mice overproduce IL-4 (first and second bars). Intestinal colonization with *B. fragilis* (third bar) reduces the expression of IL-4 from levels in OF mice. *B. fragilis* ΔPSA colonization fails to correct the $T_H2$ skew (fourth bar). Results are representative of 2 experiments from pools of 4 mice.

(B) IFN-γ expression by splenic CD4+ T during colonization indicates increased $T_H1$ cytokine production in CNV than in OF mice (first and second bars). PSA production by intestinal *B. fragilis* is required for the increase in IFN-γ expression and immune homeostasis (third bar); homeostasis is not seen in the absence of PSA (fourth bar).

(C) Intracellular cytokine staining and FC of in vitro stimulated (500 ng/mL PMA, 5 μg/mL ionomycin) cultures of splenic CD4+ T cells for 4 hours in the presence of brefeldin A shows that IFN-γ (horizontal axis) is produced specifically by CD4+ T cells (vertical axis) during bacterial colonization. PSA production by *B. fragilis* is required for the specific increase in IFN-γ expression to levels similar to those for CNV mice. OF and *B. fragilis* ΔPSA-colonized mice express low levels of $T_H1$ cytokines. Results are representative of 3 experiments with pools of 3-5 mice.

(D) Thymic histology of germ-free mice (H&E) colonized with wild-type or *B. fragilis* ΔPSA for over 1 year reveal follicles (arrows) within the inner medullary compartment in the absence of PSA. None of 5 *B. fragilis*-colonized compared to 3 of 5 *B. fragilis* ΔPSA-colonized mice displayed follicles.

(E) FC of thymic tissues recovered from groups of differentially colonized OF mice (10 per group) reveals the anomalous presence of CD19+ B cells in *B. fragilis* ΔPSA-colonized mice, a condition likely resulting from increased $T_H2$ cytokine production in the absence of PSA.

DETAILED DESCRIPTION OF THE INVENTION

It has now been found that maturation of the mammalian immune system is profoundly influenced by the specific direction of an immunomodulatory molecule expressed by the symbiotic bacteria, *B. fragilis*. This organism, a ubiquitous constituent of the mammalian lower gastrointestinal microflora, elaborates a zwitteronic polysaccharide (i.e., PSA) that directs the development of CD4+ T cells; the eventual result is the correction of immunologic defects found in the absence of bacterial colonization. Impaired systemic CD4+ T cell maturation, aberrant $T_H1/T_H2$ lineage differentiation, and defective lymphoid organ development can all be corrected by PSA or by PSA production during *B. fragilis* colonization. Dendritic cells in gut-associated lymphoid tissues (GALT) apparently sample *B. fragilis* and/or PSA from the intestine and after activation migrate to lymphoid organs and signal $T_H1$ lineage differentiation through the IL-12/STAT4 pathway. As $T_H1$ cytokine production opposes the $T_H2$ default phenotype, this process contributes to protection from disease by creating appropriate cytokine balances in the immune system.

It has been hypothesized that reduced exposure to immunomodulatory molecules of beneficial commensal bacteria that provide protection from unrelated immune diseases results from improved sanitation and antibiotic use. This "hygiene hypothesis" posits that deviations in gut microflora composition may be the environmental factor underlying development of atopy and asthma in genetically predisposed individuals.

It has now been discovered according to the invention that feeding of PSA or other zwitterionic polysaccharides having the charge characteristics of PSA to newborn infants would provide the appropriate $T_H1$ stimulus to their immune systems that would stimulate the infant to develop with a favorable $T_H1/T_H2$ balance. As described in greater detail below, the feeding of the polysaccharide can be accomplished through enteral administration of infant formulas, nutritional supplements, pills, or liquid suspensions, wherein these agents contain the isolated zwitterionic polysaccharide. In practice this can be done daily at a dose sufficient to maintain $T_H1$ stimulation over the course of the first six months to one year of life, allowing full development of a competent and healthy immune system.

Also as described in greater detail below, the polysaccharides can be PSA, PSB, or other zwitterionic polysaccharides characterized by repeating units, each repeating unit bearing a charge motif. In one embodiment, such as in PSA, the charge motif includes one positive charge and one negative charge on each repeating unit. In other embodiments, the charge motif includes at least one positive charge and at least one negative charge on each repeating unit. The positive charge is in the form of a free amino group and the negative charge is in the form of a carboxylate group, a phosphate group, or other similarly negatively charged residues.

The molecular size of the molecule to be fed could be as small as one or two saccharide units. Recent studies by the inventors have shown that a disaccharide comprised of only one non-acetylated amino sugar and one uronic acid is sufficient to stimulate T-cell proliferation. This is important because it suggests that the natural hydrolysis of these molecules which might take place in the acidic environment of the stomach would still allow carbohydrate molecules to be absorbed that remain active on the immune system.

A nutritional formula as used herein refers to a nutritional formulation suitable for enteral administration. Nutritional formulas are well known in the art and are sometimes referred to as enteral formulas. Such preparations typically include a water-based formulation containing a source of nutritional carbohydrate, amino acids and proteins, fat, vitamins, minerals, and optionally other components such as nucleic acids. In one embodiment a nutritional formula refers to an infant formula suitable for administration to human infants. The nutritional formula can be formulated and presented either as a liquid or as a dry powder for reconstitution. A nutritional formula of the invention further specifically includes at least one zwitterionic polysaccharide useful for promoting immune system maturation, as disclosed herein.

A nutritional supplement as used herein refers to a composition suitable for enteral administration either as a supplement or as an additive to any one or more components of a diet. A nutritional supplement generally can include at least one source of any one or combination of nutritional carbohydrates, amino acids and proteins, fats, vitamins, minerals, and optionally other components such as nucleic acids. In certain embodiments the nutritional supplement can be formulated and presented as a liquid, as a dry powder, as a capsule, or as a pill. Other formulations are also contemplated, including bars, sprinkles, cereals, gels, pastes, and the like. A nutritional supplement of the invention further specifically includes at least one zwitterionic polysaccharide useful for promoting immune system maturation, as disclosed herein.

A zwitterionic polysaccharide as used herein in one embodiment refers to a naturally occurring polysaccharide having certain structural features including the presence of repeating units, each with at least one positively charged moiety and at least one negatively charged moiety. A zwitterionic polysaccharide as used herein in one embodiment refers to polysaccharides that have been modified to include the structural features including the presence of repeating units, each with at least one positively charged moiety and at least one negatively charged moiety. The zwitterionic polysaccharides useful according to the invention generally have a plurality of repeating units, wherein each repeating unit comprises two to ten monosaccharides and a positively charged free amino moiety and a negatively charged moiety selected from the group consisting of carboxylate, phosphate, phosphonate, sulfate, and sulfonate. Molecular weights of the zwitterionic polysaccharides useful in the invention typically have molecular weights between 500 Da and 2,000,000 Da, although smaller and larger polysaccharides can also be used. For example, the polysachharide can be as small as one or two saccharide units. Thus a disaccharide including only one non-acetylated amino sugar and one uronic acid is sufficient to stimulate T-cell proliferation.

Polysaccharides useful according to the present invention include those naturally occurring polysaccharides that include the requisite charged groups. These polysaccharides may be derived from bacterial sources. Bacteria used as starting materials to obtain capsular polysaccharides can be obtained commercially from a number of sources. For example, the *B. fragilis*, NCTC 9343 and ATCC 23745 may be obtained from the National Collection of Type Cultures (London, England) and the American Type Culture Collection (10801 University Boulevard, Manassas, Va. 20110-2209). Polysaccharide A and polysaccharide B can be purified from the above bacteria following the protocol of Pantosti et al. (1991) Infect Immun 59:2075-2082.

In addition to the naturally occurring polysaccharides, polysaccharide repeating units that consist of at least one N-acetyl sugar and at least one uronic acid (sugar with a negatively charged carboxyl group) can be modified to produce the immune response of the present invention. A polysaccharide repeating unit containing at least one N-acetyl sugar and at least one uronic acid can be de-N-acetylated to create a free amino group and thus will yield a polysaccharide with the correct charge motif. Molecules which may be de-N-acetylated include *Salmonella typhi* capsular polysaccharide (VI antigen), *Escherichia coli* K5 capsular polysaccharide, *Staphylococcus aureus* type 5 capsular polysaccharide, Group B *Streptococcus* type III capsular polysaccharide, and *Rhizobium meliloti* exopolysaccharide II. These polysaccharides and their modification have been described in U.S. Pat. No. 5,679,654, the entire contents of which is incorporated herein by reference.

De-N-acetylation can be accomplished by conventional chemistry techniques well known to those of ordinary skill in the art. One suitable method involves the use of alkali with or without sodium borohydride. Twenty mg of polysaccharide is dissolved in 2M NaOH (3 ml) and sodium borohydride is added (50 mg). The solution is heated to 100° C. for 5 h. Following neutralization with acid, the solution is dialyzed against distilled water in the cold and freeze-dried. DiFabio, J. L, Michon, F., Brisson, J. R., Jennings, H. J., Weasels, M. R. Benedi, V. J., Kasper, D. L. (1989) Structure of the capsular polysaccharide antigen of type IV groups B *Streptococcus*. Can J Chem 67:877-882.

Bacterial polysaccharides which possess imine groups (C=NH) in addition to free carboxyl groups may be modified and used to produce the immune response of the present invention. Many of the *Pseudomonis aeruginosa* O-specific side chains possess imine groups. Imine groups can be reduced with sodium borohydride ($NaBH_4$) to create free amino groups ($NH_3^+$). An example of a compound which may be reduced with sodium borohydride to create free amino groups is *Pseudomonas aeruginosa* Fisher 7.

A bacterial capsular polysaccharide as used herein refers to a polysaccharide which occurs in nature as a component of the capsule of a bacterial cell. For use in the present invention, a bacterial capsular polysaccharide is isolated from the bacterial cell in which it occurs in nature. As used herein, isolated means removed from other components with which a polysaccharide may be found in nature.

A naturally occurring bacterial capsular polysaccharide as used herein refers to a bacterial capsular polysaccharide that is not modified from how it occurs in nature except for being isolated.

*B. fragilis* polysaccharide A (PSA) as used herein refers to *B. fragilis* capsular polysaccharide A as disclosed, for example, in U.S. Pat. No. 5,679,654. This polysaccharide has a tetrasaccharide repeating unit containing one cationic free amine and one anionic carboxylate in each repeating unit.

Tzianabos A O et al. (1992) *J Biol Chem* 267:18230-5; U.S. Pat. Nos. 5,679,654 and 5,700,787. PSA is also known as PSA1.

PSA2 as used herein refers to *B. fragilis* capsular polysaccharide A as disclosed, for example, in Wang Y et al. (2000) *Proc Natl Acad Sci USA* 97:13478-83, and Kalka-Moll W M et al. (2001) *Infect Immun* 69:233944. *Bacteroides fragilis* PSA2 has a pentasaccharide repeating unit containing mannoheptose, N-acetylmannosamine, 3-acetamido-3,6-dideoxyglucose, 2-amino-4-acetamido-2,4,6-trideoxygalactose, fucose, and 3-hydroxybutanoic acid. PSA2 is zwitterionic and carries one cationic free amine and one anionic carboxylate in each repeating unit.

*B. fragilis* polysaccharide B (PSB) as used herein refers to *B. fragilis* capsular polysaccharide B as disclosed, for example, in U.S. Pat. No. 5,679,654. This polysaccharide has a repeating unit that includes six monosaccharides.

*Shigella sonnei* Phase I lipopolysaccharide O-antigen, *Streptococcus pneumoniae* type 1 capsular polysaccharide, and *Streptococcus pneumoniae* group antigen C substance are additional zwitterionic polysaccharides disclosed for example in U.S. Pat. No. 5,679,654 and useful in the instant invention.

Immune system maturation as used herein refers to development of an immune system characterized by a $T_H1/T_H2$ balance that is associated with a healthy adult phenotype. A healthy adult phenotype is to be contrasted with a default $T_H2$ phenotype that is characteristic of atopy, allergic asthma, or certain types of autoimmune disease. Immune system maturation can be assessed by measuring, either at a single point in time or serially over a relevant span of time, relative contributions of at least one $T_H1$ marker and at least one $T_H2$ marker.

An infant as used herein refers to a human less than 12 months old. In one embodiment an infant is 0-9 months old. In one embodiment an infant is 0-6 months old. In one embodiment an infant is 0-3 months old.

As used herein, enterally has its usual meaning and refers to any route involving administration to at least one component of a gastrointestinal tract. Enteral administration can be accomplished by any suitable method, including oral feeding (e.g., sucking, chewing, swallowing); nasogastric delivery; orogastric delivery; gastric delivery; duodenal, jejunal, or other small intestinal delivery; enema and other forms of delivery to the large intestine. In one embodiment enterally refers to orally.

A T helper 1 marker ($T_H1$ marker) as used herein refers to an objectively measurable manifestation of a $T_H1$ immune phenotype. $T_H1$ markers include, without limitation, certain cytokines including interferon gamma (IFN-γ) and interleukin 2 (IL-2), as well as certain immunoglobulin isotypes, e.g., IgG1 in humans and IgG2a in mice. Methods for measuring $T_H1$ cytokines and immunoglobulin isotypes are well known in the art and can include, without limitation, appropriate cytokine-specific or isotype-specific enzyme-lined immunosorbent assay (ELISA), bioassay, quantitative reverse transcriptase-polymerase chain reaction, and the like.

A T helper 2 marker ($T_H2$ marker) as used herein refers to an objectively measurable manifestation of a $T_H2$ immune phenotype. $T_H2$ markers include, without limitation, certain cytokines including interleukin 4 (IL-4) and interleukin 5 (IL-5), as well as certain immunoglobulin isotypes, e.g., IgE in humans and in mice. Methods for measuring $T_H2$ cytokines and immunoglobulin isotypes are well known in the art and can include, without limitation, appropriate cytokine-specific or isotype-specific ELISA, bioassay, quantitative reverse transcriptase-polymerase chain reaction, and the like.

An increase in a T helper 1 marker to a T helper 2 marker as used herein refers to skewing a T helper subtype predominance toward a $T_H1$ phenotype and/or away from a $T_H2$-dominant phenotype, e.g., away from a $T_H2$ default phenotype. Any increase in the ratio of $T_H1$ to $T_H2$ results in an increase in a T helper 1 marker to a T helper 2 marker. In one embodiment such increase can be measured at a single point in time, with reference made to some standard or control. Alternatively or in addition, in one embodiment such increase can be measured serially over a relevant span of time, comparing results from one time point to results from another time point, for a single subject. Methods for measuring $T_H1$ markers and $T_H2$ markers are as described above.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Experimental Procedures

Mice and Bacterial Strains

Conventional specific pathogen-free (SPF) mice of strains C57BL/6NTac, BALB/cAnNTac, B6.SJL-Ptprc$^a$/BoAiTac-H2-Ab1$^{tm1GLM}$ N13 (MHCII$^{-/-}$), and B6.SJL-Ptprc$^a$/BoAiTac (MHCII$^{-/-}$ control) were purchased from Taconic Farms (Germantown, N.Y.). C.129S2-Stat4$^{tm1Gru}$ (Stat4$^{-/-}$) mice were purchased from Jackson Laboratory (Bar Harbor, Me.). These mice were housed in conventional cages at Harvard Medical School (HMS). Germ-free Swiss-Webster mice were from Taconic Farms and housed in sterile isolators (Class Biologically Clean, Madison, Wis.). Mice were screened weekly for bacterial, viral, and fungal contamination. All procedures with mice were performed according to guidelines of the HMS Office for Research Subject Protection.

*B. fragilis* strain NCTC 9343 and its isogenic PSA deletion mutant have been described (Coyne et al., 2001). For mouse colonization, ~1×10$^8$ CFU of bacteria grown in BHI medium were spread on food and bedding. Mice were colonized for at least 60 days before examination. Results are for mice up to 8 months post-colonization (except thymic pathology, which requires aging over 1 year).

Lymphocyte Isolation from Tissues

Lymphocytes were isolated from tissues (Tzianabos et al, 2000). In brief, spleens, thymuses, and MLNs were disrupted into single-cell preparations, and enriched for lymphocytes over a Histopaque® 1083 gradient, (a solution of polysucrose and sodium diatrizoate (Sigma, St. Louis). Cells were washed with PBS and used directly or fixed with 0.5% PFA for 1 hour at 4° C.

Flow Cytometry, Fluorescence-Activated Cell Sorting and Intracellular Cytokine Staining Directly fluorochrome-conjugated monoclonal antibodies were used (BD Pharmingen, San Diego). For surface staining, lymphocyte preparations were washed twice in FC buffer (PBS with 2% FBS) and resuspended in 100 μL. 1×10$^6$ cells were incubated with antibodies at 2 μg/mL for 30 min at 4° C. For intracellular cytokine staining, cells were resuspended in 100 μL of CYTOFIX/CYTOPERM™ (BD Biosciences, San Diego) buffer for 30 min at 4° C., washed with PERM/WASH™ (BD Biosciences, San Diego) buffer, and incubated with fluorochrome-conjugated anti-cytokine antibodies for 30 min at 4° C. Cells were washed and analyzed on a model FC500 Cytometer (Beckman Coulter, Fullerton, Calif.), and all data were analyzed with RXP Analysis Software (Beckman Coulter). FACS was performed on a BD FACSARIA™ (BD Biosciences, San Diego), and cell purity was always >99%.

PSA Purification and Animal Treatment

PSA from B. fragilis NCTC 9343 was prepared as previously described (Tzianabos et al, 1992). For some studies, PSA was treated with acetic anhydride to neutralize the positively charged amino group (Tzianabos et al., 1994). Mice received 50 µg of PSA in 1.5% sodium bicarbonate/PBS intraperitoneally or intragastrically 3 times a week for 2 weeks. Rag2$^{-/-}$ mice received 30 µg of PSA (PBS controls) in alternating intragastric and subcutaneous treatments 3 times a week.

In Vitro Cytokine Stimulation and Proliferation Assays

For analysis of splenic cytokines, lymphocytes were isolated as above. CD4$^+$ T cells were purified with the MACS® CD4 Sorting Kit (Miltenyi Biotec, Auburn, Calif.). Cell purity was >97% CD4$^+$. The remaining lymphocytes were used as APCs after gamma-irradiation. $3 \times 10^5$ cells of each type were mixed in a 48-well plate, and anti-CD3/anti-CD28 (2 µg/mL) was added. Supernatants recovered after stimulation for 48 and 72 hours were analyzed by ELISA.

For co-cultures, CD4$^+$ T cells were purified from splenic lymphocytes with a CD4$^+$ T Cell Subset Kit (R&D Systems). Cell purity was >95%. BMDCs from femurs of mice were purified. Cells were cultured for 8 days in C—RPMI-10 with GM-CSF (20 ng/mL; Biosource, Camarillo, Calif.). Cells were >90% CD11c$^+$. $1 \times 10^6$ purified CD4$^+$ T cells were mixed with $1 \times 10^6$ purified CD11c$^+$ BMDCs and incubated at 37° C./5% $CO_2$.

ELISA plates were from precoated kits (Biosource). T-cell proliferation assays were done with $1 \times 10^5$ cells of each type (APCs irradiated) after incubation for 96 hours. For the last 8 hours before harvest, wells were pulsed with [$^3$H]thymidine (1 µCi/well). Cells were washed, harvested and counted by liquid scintillation (Wallac; now PerkinElmer, Boston). Data were expressed as mean cpm ±SD for triplicate wells.

Histological Tissue Analysis

Paraffin-embedded mouse tissues were stained with H&E. Sections were evaluated in blinded fashion by a single pathologist (R. T. Bronson, H M S).

Example 1

Mono-Colonization of Germ-Free Animals with B. fragilis Results in CD4$^+$ T Cell Expansion The effects of bacterial colonization on immune maturation in animals were investigated, exploring the role of the microbial flora in systemic T cell development. Germ-free mice, animals born and raised in sterile isolators devoid of microbes, were used. Initially, spleens were harvested from both conventionally colonized and germ-free mice and were analyzed for total CD4$^+$ T cells by flow cytometry (FC). All groups of mice had similar splenic total lymphocyte counts (average: $1 \times 10^8$). Consistent with seminal observations of a positive immunologic role of autochthonous bacteria (Dobber et al., 1992), the lymphocyte population purified from spleens of conventional SPF (specific pathogen-free) mice with a diverse gut microflora contained a greater proportion of CD4$^+$ T cells than that of germ-free mice (FIG. 1A). Previous studies have documented the beneficial role of commensal bacteria in intestinal development (Hooper, 2004). The observed alteration in CD4$^+$ T cell proportions of splenic lymphocytes highlights the profound effects of bacterial colonization of the gut on the systemic immune response.

Figure 1B:
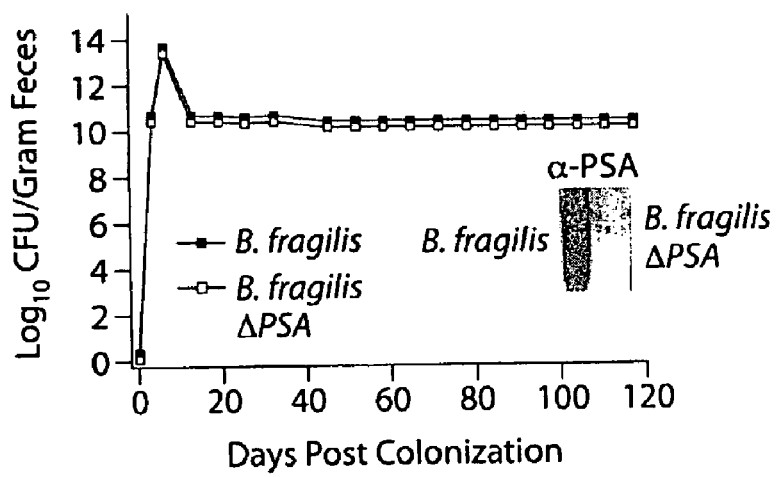
Figure 1C:
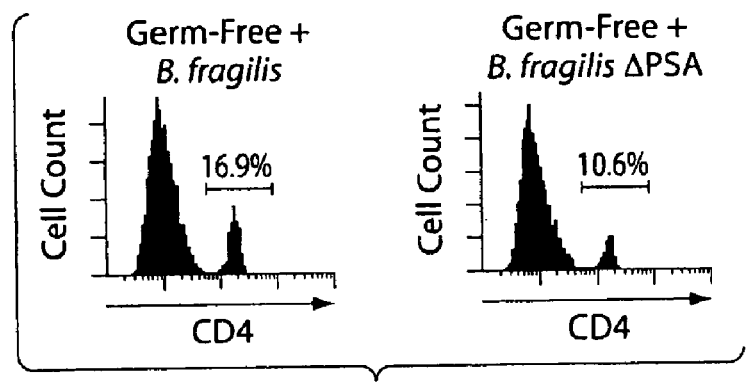

SPF mice harbor a diverse and complex microbial flora. To stringently investigate the influence of specific bacterial constituents of the gut flora on the host immune system, germ-free mice were colonized with a single bacterial species. This approach allows "real-time" measurements of responses to bacterial colonization in animals with a naïve immune system. The model microorganism B. fragilis was chosen because of its prominence in the normal microbial gut flora and its production of known immunomodulatory molecules (Kononen et al., 1992; Tzianabos and Kasper, 2002). In the absence of competing bacterial species, germ-free mice mono-associated with B. fragilis strain NCTC 9343 were readily colonized to high levels (>$10^{10}$) CFU/g of feces; FIG. 1B). Flow cytometry of splenic lymphocytes from these mice showed a nearly complete restoration of CD4$^+$ T cells to conventional proportions (FIG. 1A and FIG. 1C). Thus B. fragilis mono-colonization was sufficient to correct CD4$^+$ T cell deficiency in spleens of germ-free mice. No other bacterial species alone has been shown to correct lymphoid defects in germ-free animals (Cash and Hooper, 2005).

Example 2

Immunomodulatory Effects of B. fragilis Require Production of PSA

At least 2 of the 8 capsular polysaccharides of B. fragilis are ZPSs, a unique class of bacterial molecules with immunomodulatory properties (Tzianabos and Kasper, 2002). We wondered whether PSA, the most immunodominant and highly conserved ZPS, plays a role in splenic T cell expansion during B. fragilis commensalism. PSA-deficient B. fragilis ΔPSA were used to mono-colonize germ-free mice (Coyne et al., 2001). The level of intestinal colonization by the mutant was indistinguishable from that by the isogenic parent strain, as assessed by fecal CFU counts (FIG. 1B). Examination of splenic lymphocyte populations from mice colonized with B. fragilis lacking PSA but expressing all other antigens produced by this organism revealed an inability to correct CD4$^+$ T-cell deficiencies in germ-free mice (FIG. 1C). In pooled experiments (n=4), the average proportions of CD4$^+$ T cells were: Conventional: 17.82%±2.1; B. fragilis: 18.05%±1.9; B. fragilis ΔPSA: 10.95%±2.3; and Germ-free: 11.15%±1.5. The effects were specific to CD4$^+$ T cells, as the proportions of CD8$^+$ T cells and CD19$^+$ B cells from splenic lymphocytes (FIG. 1D) were indistinguishable between conventional and either mono-colonized or germ-free mice, as previously observed (Pereira et al, 1986). Together, these results show that B. fragilis colonizing the gut of germ-free mice requires PSA production to correct host systemic CD4$^+$ T cell deficiencies during commensalism.

Example 3

PSA Production by B. fragilis Directs Lymphoid Organogenesis

Figure 1D:
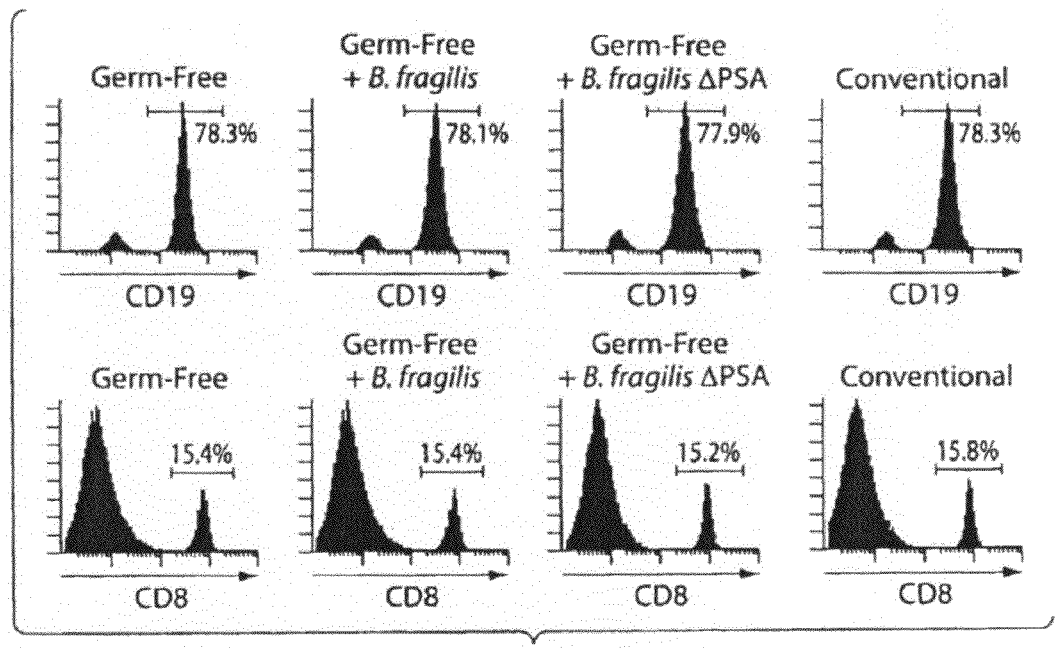
Figure 1E:
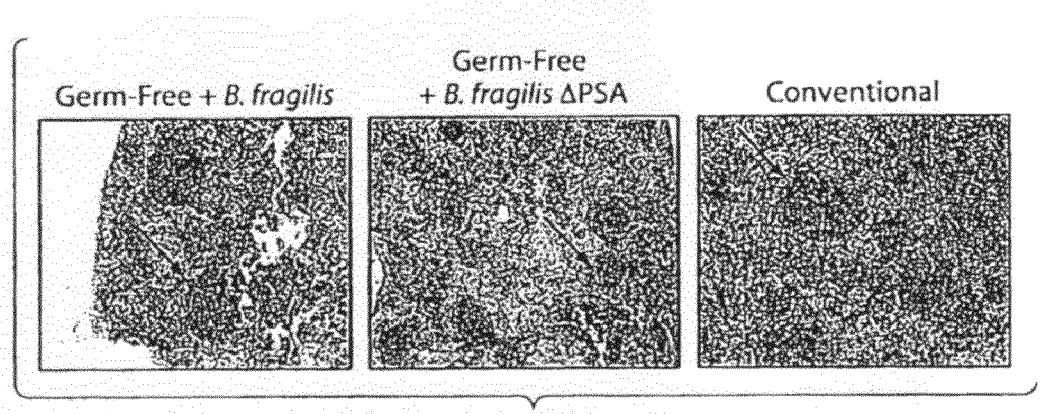

Commensal bacteria have long been appreciated for their positive impact on development of gut-associated lymphoid tissues (GALT, including Peyer's patches) and intraepithelial lymphocytes (IELs) and production of mucosal IgA (Hooper, 2004). The experiments in this example examined whether cellular immune maturation after bacterial colonization was also manifested in the morphological and ultrastructural development of peripheral lymphoid tissues. Germ-free animals have recently been reported to display defects in splenic structural development (Macpherson and Harris, 2004). Histological sections of spleens from germ-free mice colonized with wild-type *B. fragilis* or *B. fragilis* ΔPSA were examined. Spleens from mice mono-colonized with *B. fragilis* appeared normal, with well-formed lymphocyte zones appearing as defined follicles (white pulp) similar to those in conventional mice with a complete gut flora (FIG. 1E). The interspersed red pulp was densely packed with red blood cells and neutrophils. Spleens from germ-free mice colonized with *B. fragilis* ΔPSA showed gross anatomical depletion of the lymphocyte zones similar to that in uncolonized germ-free mice (Macpherson and Harris, 2004). Follicles were smaller, less defined, and more fragmented than in germ-free mice colonized with wild-type *B. fragilis* or conventional mice (FIG. 1E). The overall size and shape of spleens from all groups were comparable. This finding suggests a role for PSA specifically in lymphocyte development. Thus changes in CD4$^+$ T cell expansion that are mediated by PSA produced by intestinal bacteria are consistent with the correction of physical and developmental defects in secondary lymphoid tissues. This observation reflects the importance of the beneficial relationship between commensal microorganisms and host physiology.

Example 4

Figure 2A:
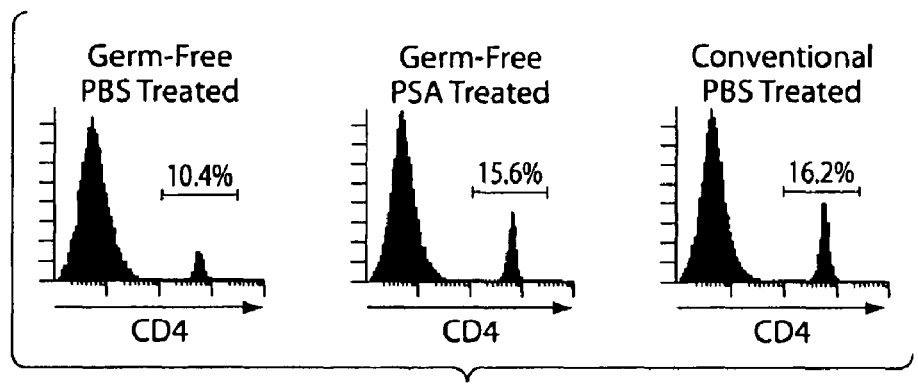
Figure 2B:
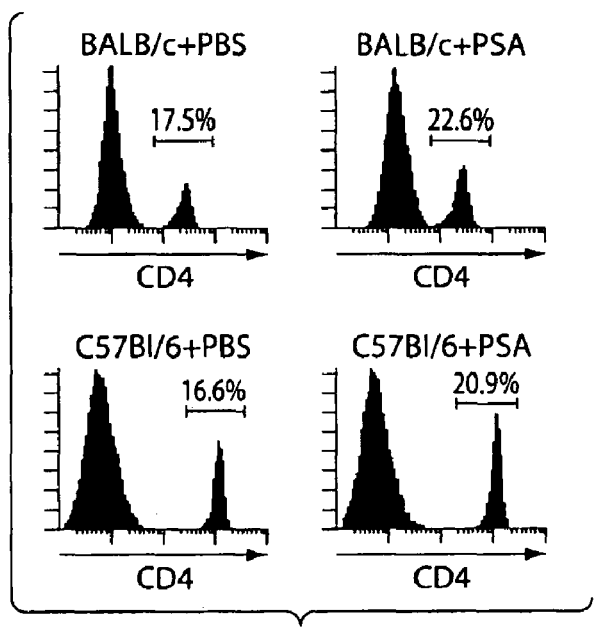
Figure 2C:
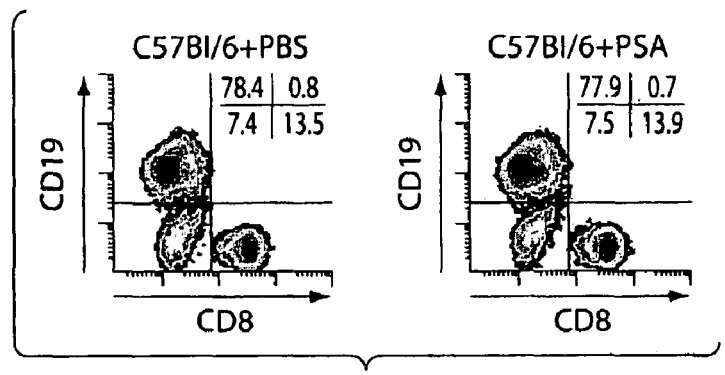

Purified PSA is Sufficient to Expand T Cells in Germ-Free and Conventional Animals The inability of a PSA-deficient mutant to cause T-cell expansion showed that the activity of this immunomodulatory molecule is required during *B. fragilis* colonization. Using chromatography to purify PSA extracted from the surface of *B. fragilis*, it was investigated whether PSA alone is sufficient to counter the CD4$^+$ T cell defects in germ-free mice. Purity was assessed by various methods, including H$^1$-NMR, spectroscopy, and gel electrophoresis. The preparation was devoid of contamination by protein, nucleic acid, and endotoxin (LPS). Uncolonized germ-free mice were treated intraperitoneally with purified PSA and then assessed for splenic T cell expansion. Purified PSA was found to restore CD4$^+$ T cell proportions among splenic lymphocytes in germ-free mice to conventional levels (FIG. 2A).

To assess whether the route of administration to mice of various backgrounds affects PSA's immunomodulatory properties, both conventionally colonized C57BL/6 and BALB/c mice received purified PSA intragastrically. This treatment recapitulates intestinal exposure of animals to PSA during colonization. Oral treatment led to a specific increase of splenic CD4$^+$ T cells in conventional mice (FIG. 2B), showing that PSA's effect is not exclusive to germ-free animals. CD8$^+$ T cell and CD19$^+$ B cell ratios were unaffected by PSA (FIG. 2C) as formerly shown (FIG. 1D). These studies demonstrated that specific recognition of purified PSA by host immune components in the intestines resulted in splenic CD4$^+$ T cell expansion.

In further experiments germ-free mice are administered purified PSA intragastrically. Effects of oral treatment of germ-free mice is assessed by measurement JO of splenic CD4$^+$ T cells, CD8$^+$ T cell and CD19$^+$ B cell ratios, and $T_H1$ (e.g., IFN-γ) and $T_H2$ (e.g., IL-4) cytokine production.

Example 5

Figure 3A:
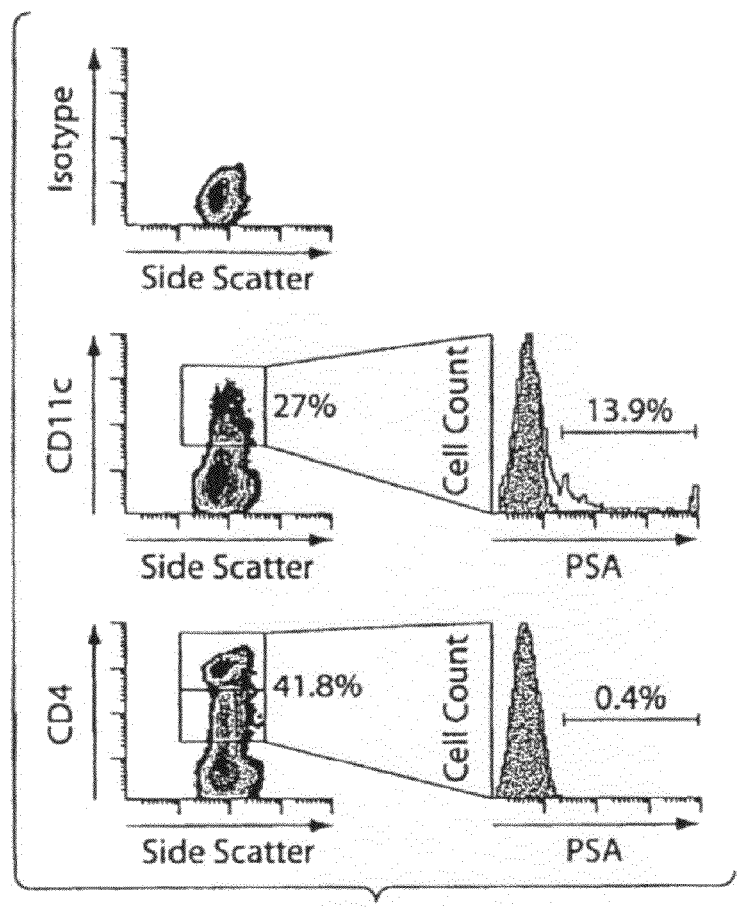
Figure 3B:
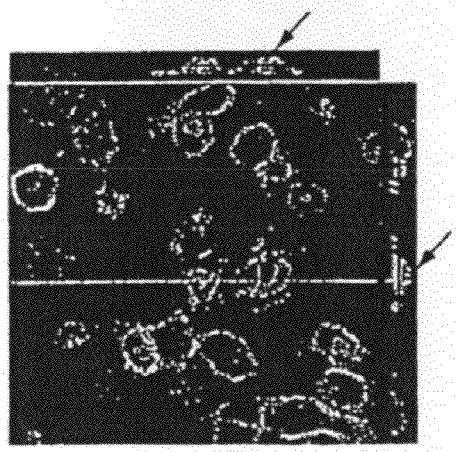
Figure 3C:
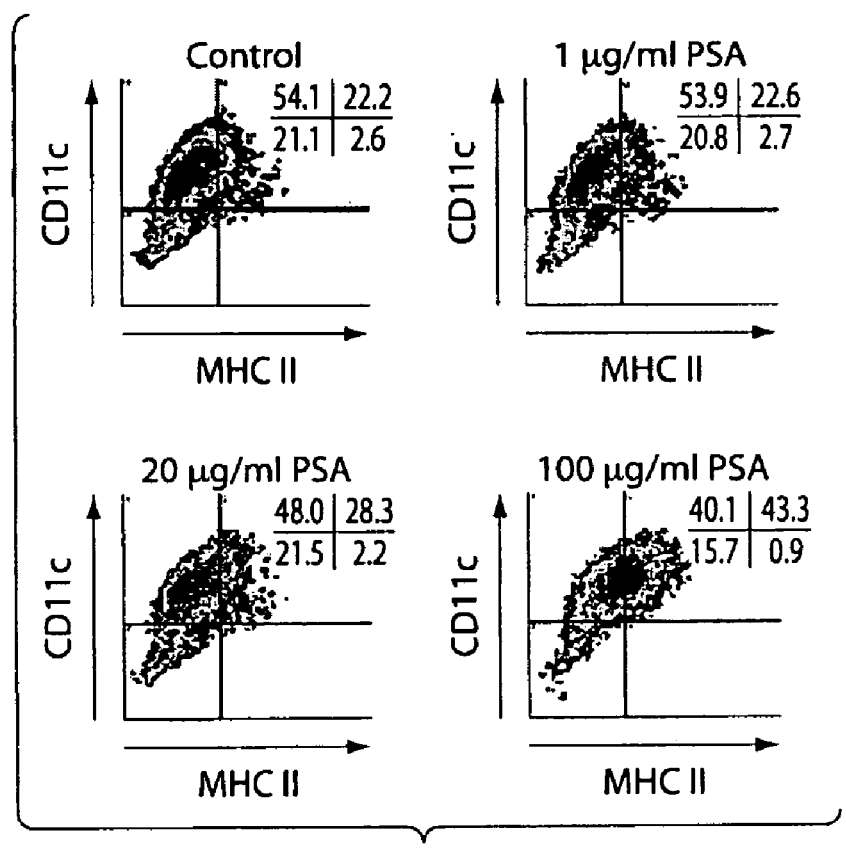
Figure 3D:
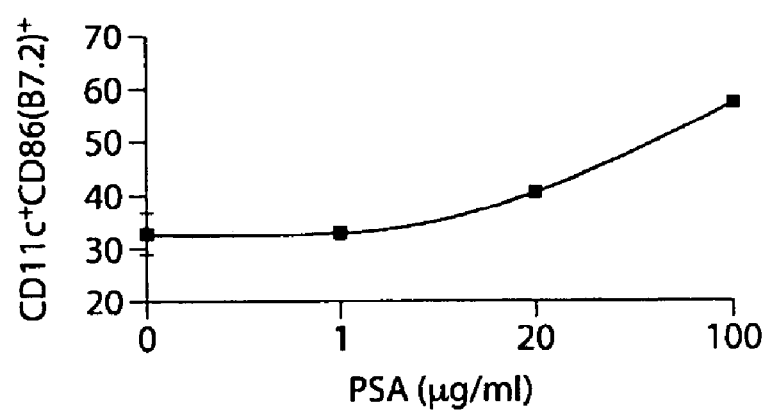

PSA is Specifically Recognized by Dendritic Cells, with Consequent Cell Activation All CD4$^+$ T cell reactions require instruction to T cells by APCs (Kidd, 2003; Kapsenberg, 2003). PSA is recognized by APCs and then presented to T cells in vitro (Kalka-Moll et al., 2002). The cellular mechanism of PSA recognition in the intestine and subsequent signaling to expand splenic T cells is unknown. To characterize the APC responsible for PSA effects in animals, mice were fed fluorescently labeled PSA by gavage and then cells were recovered from mesenteric lymph nodes (MLNs). As shown by flow cytometry, PSA specifically associated with CD11c$^+$ dendritic cells (DCs; FIG. 3A), and not with CD4$^+$ T cells or CD19+ B cells (FIG. 3A and data not shown) in the MLNs. The notion of in vivo DC recognition of PSA appears appropriate, as DCs are the only APCs known to sample luminal contents from the intestine and migrate to lymph nodes to initiate T cell reactions (Rescigno et al., 2001; Mowat, 2003). Consistent with this hypothesis, no PSA was recovered from spleens of orally treated mice despite splenic T cell expansion. In addition, confocal microscopy revealed that PSA was internalized by primary cultured bone marrow-derived DCs (BMDCs) and was subsequently displayed on the cell surface (FIG. 3B). Thus it appears that DCs sample intestinal PSA by antigen uptake and migrate only as far as the local lymph nodes. These results agree with those of Macpherson and Uhr (2004), who observed that commensal bacteria are internalized by intestinal DCs that migrate to MLNs only.

We next assessed whether the association of PSA with BMDCs leads to cell activation and maturation, as only mature DCs can activate T cells. PSA-mediated maturation of DCs was measured by up-regulation of MHC II among CD11c$^+$ cells from 22% to 43% after PSA treatment (FIG. 3C), a process required for efficient antigen display to the receptor on CD4$^+$ T cells (Banchereau and Steinman, 1998; Thery and Amigorena, 2001). Treatment also increased expression of the costimulatory molecules CD80 (B7.1) and CD86 (B7.2) in a dose-dependent manner (data not shown and FIG. 3D, respectively), a result further showing that PSA interacts with and induces maturation of DCs. These findings are consistent with the observation that DCs, not B cells, mediate intestinal antigen presentation to T cells after conventionalization of germ-free animals (Yamanaka et al., 2003).

Example 6

PSA Induces T-Cell Proliferation when Presented by DCs In Vitro

To further investigate cellular and molecular events underlying immune responses to PSA, an in vitro co-culture system using primary cells to assess the ability of purified PSA to induce T-cell proliferation and cytokine expression was developed. As shown above, PSA treatment led to CD4$^+$ T cell expansion in mice. Incubation of PSA with CD11c$^+$ BMDCs and naïve splenic CD4$^+$ T cells led to a dose-dependent increase in T-cell proliferation (FIG. 4A). Neutralization of the positive charge by chemical modification of PSA (N-acetylated [NAc] PSA) resulted in no incorporation of [$^3$H]thymidine-a marker for cell replication. This extends to DCs our observation that the zwitterionic structure of PSA is critical for biological activity (Kalka-Moll et al., 2002; Tzianabos and Kasper, 2002). Purified *E. coli* LPS did not induce T-cell proliferation in mice (FIG. 4A; LPS). PSA-mediated CD4$^+$ T-cell proliferation required both DCs and T cells; either cell type alone resulted in no incorporation of radiolabel (FIG. 4A). Together, these results show that DCs can direct T-cell proliferation in response to purified PSA in vitro.

Example 7

PSA Induces T Cell Cytokine Production in Dendritic Cell Co-Cultures

The two subtypes of effector CD4$^+$ T cells, T$_H$1 and T$_H$2, are defined by expression of the cytokines interferon γ (IFN-γ) and interleukin 4 (IL-4), respectively (Janeway et al., 2001). As shown above, PSA induces CD4$^+$ T cell expansion in B. fragilis-colonized mice and in vitro. To further characterize the effects of PSA-mediated T cell activation, cytokine profiles using purified cellular components were assessed. Co-culture of DCs and CD4$^+$ T cells in the presence of PSA yielded dose-dependent up-expression of the T$_H$1 cytokine IFN-γ (FIG. 4B). The level of IFN-γ production associated with PSA was comparable to that associated with several known potent IFNiγ inducers (anti-CD3, LPS, and staphylococcal enterotoxin A [SEA]) and required both DCs and T cells (FIG. 4B). Specificity was evidenced by the lack of T$_H$1 cytokine production after NAc-PSA treatment (FIG. 4B).

Figure 4C:
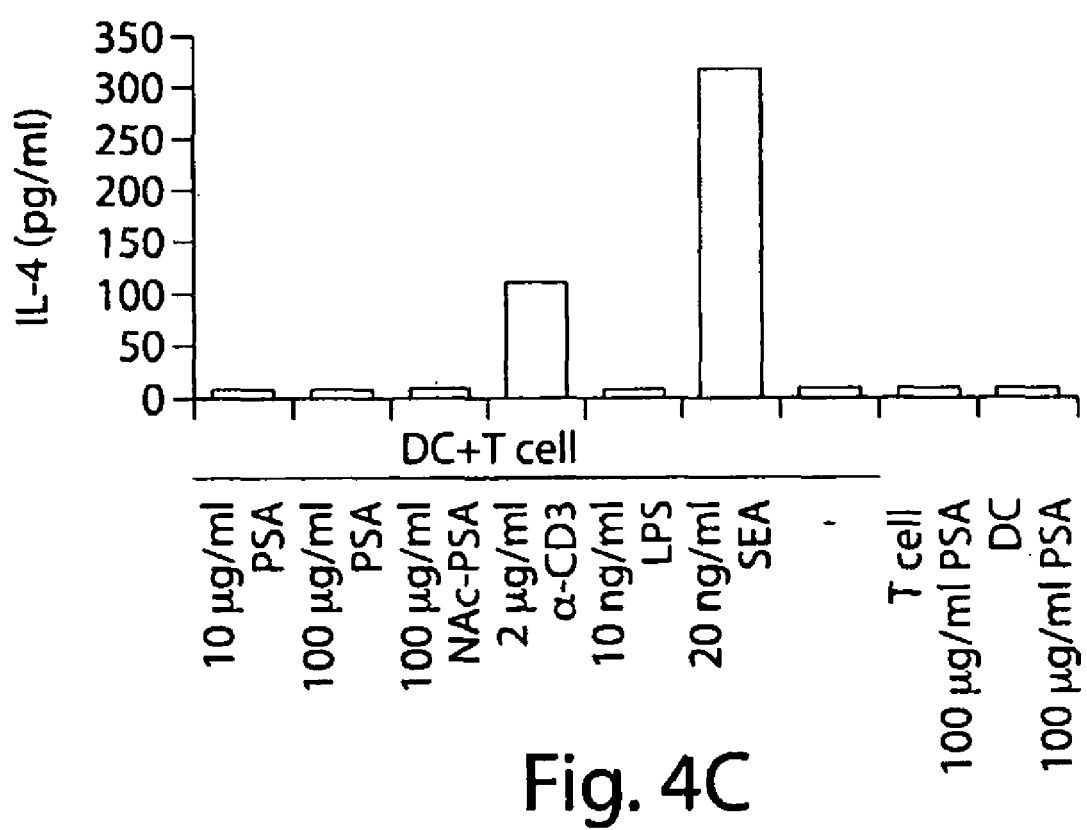

T$_H$1 cytokine production suppresses T$_H$2 responses; conversely, T$_H$2 cytokine expression inhibits T$_H$1 responses. Normal immune responses require a controlled balance of these opposing signals. Examination of IL-4 expression in response to PSA treatment revealed no cytokine production by purified CD4$^+$ T cells (FIG. 4C; 100 μg/ml PSA). Anti-CD3 and the superantigen SEA are potent stimulators of both classes of cytokine (FIG. 4C). As T$_H$2 cytokine production is a "default pathway" in many systems (Kidd, 2003; Amsen et al. 2004) and T$_H$1 cytokine production is antagonistic to T$_H$2 expression, the specific stimulation of IFN-γ by PSA in vitro may provide a mechanism for establishing commensal-mediated homeostasis of the host immune system by balancing T$_H$1/T$_H$2 responses.

Example 8

Figure 5A:
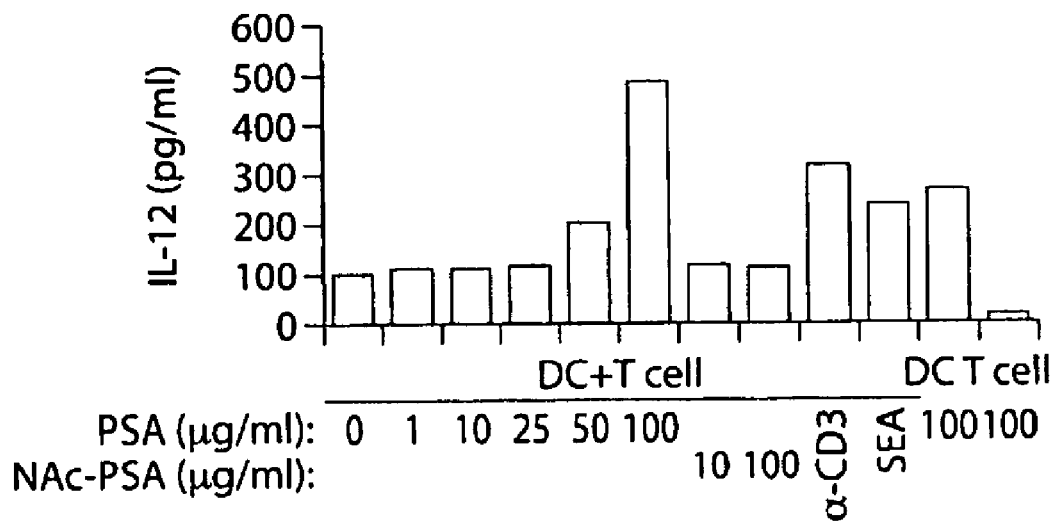
Figure 5B:
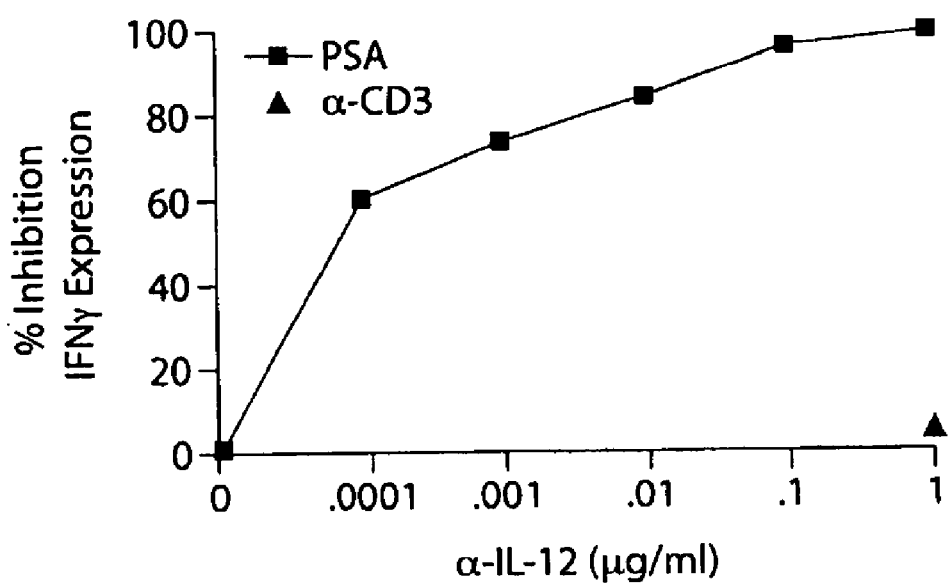
Figure 5C:
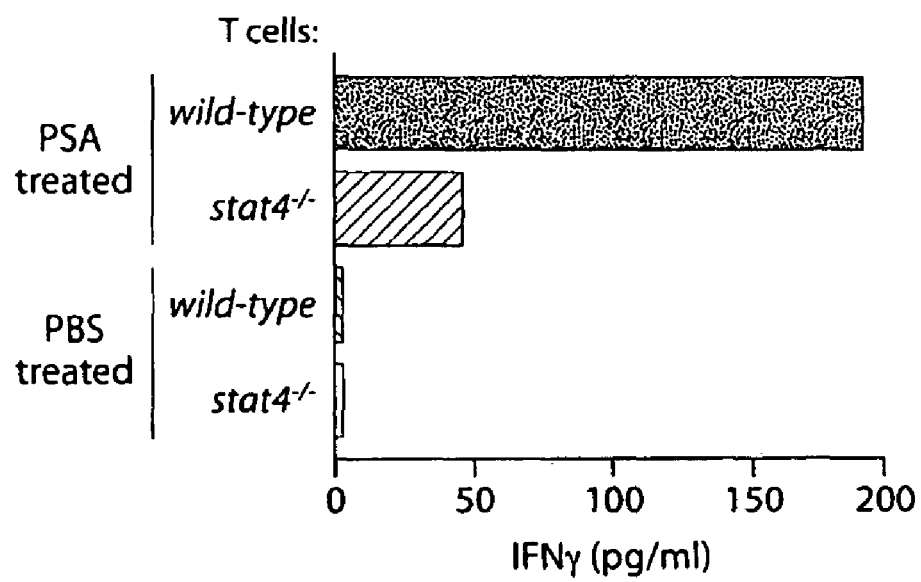

T$_H$1 Cytokine Production in Response to PSA Treatment Requires Signaling Through the IL-12/Stat4 Pathway and MHC II Expression A unique immunologic molecule, PSA is the only carbohydrate studied to date that is internalized into APCs and displayed by MHC II to T cells (Cobb et al., 2004)—a process previously believed to be reserved for protein antigens. We further characterized the molecular pathway for PSA-induced T$_H$1 cytokine production Many of the molecular signaling events involving T-helper cytokine expression are well characterized. The major pathway of IFN-γ up-regulation and T$_H$1 cell differentiation involves DC secretion of IL-12, which binds to the IL-12 receptor on T cells and signals to activate the T$_H$1-specific transcription factor Stat4 (Trinchieri, 2003). PSA stimulation of DC-T cell co-cultures elicited a dose-dependent increase in IL-12 production (FIG. 5A). DCs alone stimulated with PSA secreted IL-12 (FIG. 5A, DC 100 μg/ml PSA), although at levels lower than those found for CD4$^+$ T cells. This is the first bacterial polysaccharide shown to signal IL-12 secretion by APCs, as previously shown for classical protein antigens (Macatonia et al., 1995). NAc-PSA, lacking the essential positive-charge motif, did not stimulate cytokine production. To determine whether IL-12 is required for T$_H$1 cell differentiation, IFN-γ expression we measured after PSA treatment in the presence of increasing concentrations of neutralizing antibody to IL-12 (Heufler et al, 1996). IL-12 neutralization abolished PSA-mediated IFN-γ secretion by CD4$^+$ T cells In vitro (FIG. 5B). Ablation of IL-12 signaling does not affect anti-CD3-mediated IFN-γ expression, as this signal is APC-independent, acting directly on T cells. To determine whether IL-12 signaling that results in T$_H$1 lineage differentiation involves the Stat4 transcription factor, DCs from wild-type mice were incubated with CD4$^+$ T cells from stat4 knockout mice and IFN-γ expression in response to PSA treatment was measured. The absence of Stat4 greatly reduced T$_H$1 cytokine production (FIG. 5C); thus PSA specifically induced DCs to signal T cell differentiation through Stat4 transcriptional regulation.

Figure 5D:
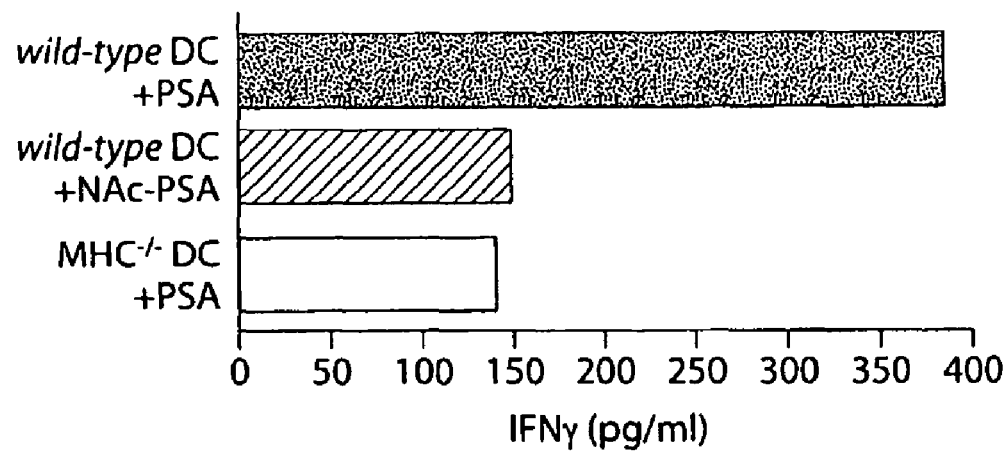

To investigate whether antigen presentation of PSA was required for cytokine signaling, DCs were purified from MHC II-deficient mice and DC-T cell co-cultures were treated with PSA or NAc-PSA. The level of IFN-γ expression was significantly higher in wild-type (MHC II$^{+/+}$) mice treated with PSA than in MHC II knockout mice (MHC II$^{-/-}$), which expressed amounts similar to a NAc-PSA control (FIG. 5D). Together, these results demonstrate that T$_H$1 cytokine responses to PSA require MHC II expression by APCs and involve signaling through the IL-12/Stat4 pathway to induce T cell activation and proper cytokine expression.

Example 9

Figure 6A:
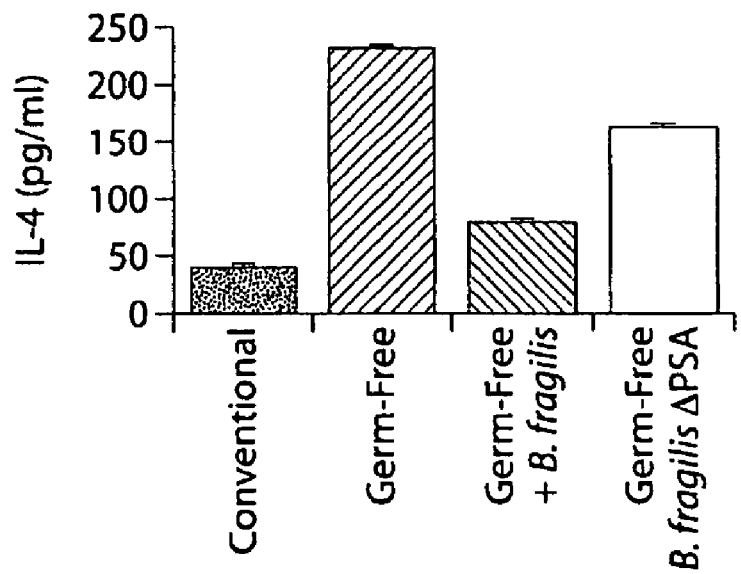

PSA is Required for Appropriate CD4$^+$ T-Helper Cytokine Production During Colonization A proper T$_H$1/T$_H$2 balance is critical for human and animal health; over- or underproduction of either response is associated with immunologic disorders. The effects of PSA on T$_H$1/T$_H$2 cytokine responses in colonized animals were investigated, again using germ-free mice. CD4$^+$ T cells from mouse spleens were purified and tested by ELISA for cytokine production. FIG. 6A shows overproduction of the T$_H$2 cytokine IL-4 in spleens of germ-free mice compared with levels in conventional mice. This result is consistent with previous reports of the appreciably T$_H$2-skewed profile of mice devoid of bacterial contamination and reflects the human neonatal (precolonization) cytokine profile (Kirjavainen and Gibson, 1999; Prescott et al., 1998; Adkins, 2000; Kidd, 2003). This "default" T$_H$2-bias in the absence of bacterial colonization again highlights the profound contributions of the microflora to immune development and provides a model to test the effects of symbiotic bacteria on the establishment of appropriate host cytokine production.

Mice colonized with wild-type B. fragilis alone displayed a level of IL-4 production similar to that in conventional mice with a complex microflora (FIG. 6A); this similarity shows the organism's sufficiency to correct systemic immune defects. Moreover, mice colonized with B. fragilis ΔPSA produced T$_H$2 cytokines at elevated levels, similar to those in germ-free mice (FIG. 6A). Thus the expression of a single bacterial antigen allows B. fragilis to correct the IL-4 cytokine imbalance found in uncolonized animals.

Figure 6B:
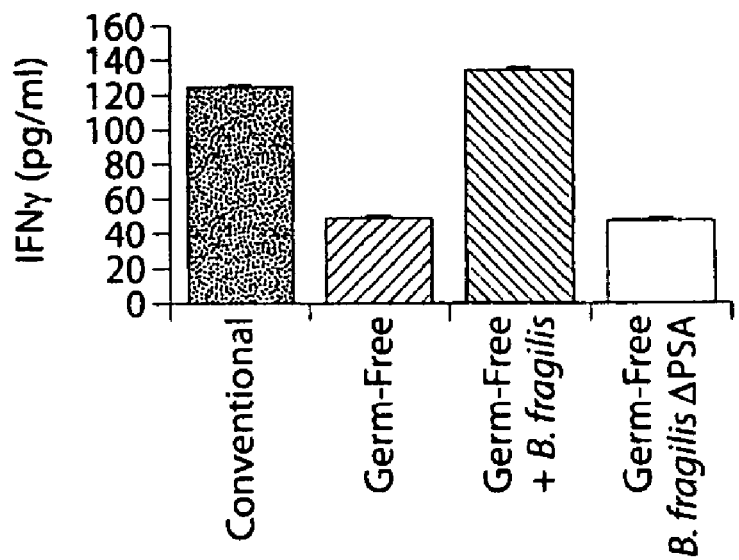
Figure 6C:
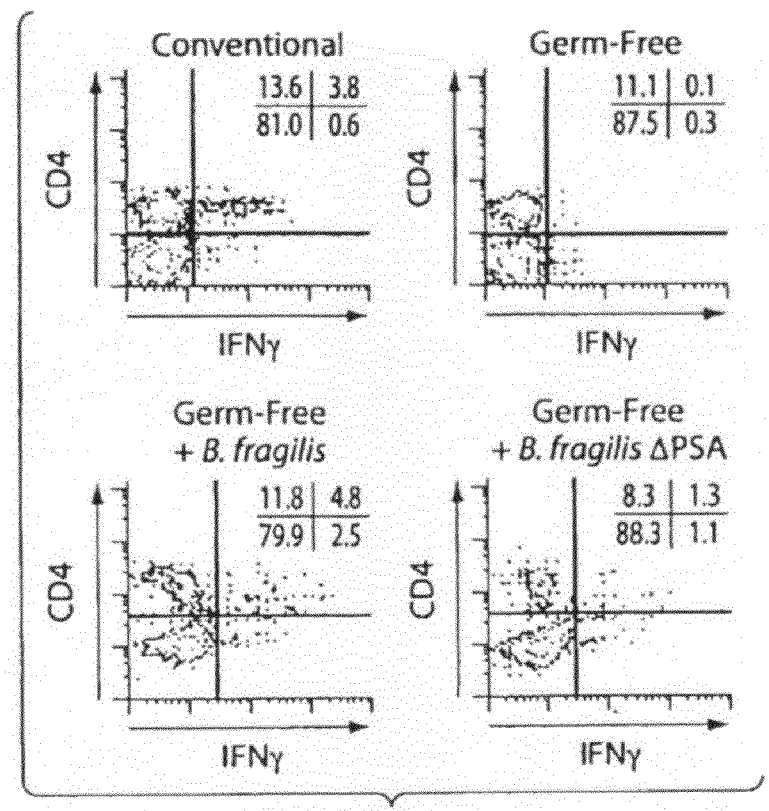

Examination of IFN-γ production by purified splenic CD4$^+$ T cells revealed that germ-free mice, which are T$_H$2-skewed, were deficient in production of this prototypical T$_H$1 marker when compared to conventional mice (FIG. 6B). Colonization with wild-type B. fragilis alone was sufficient to correct the defect in IFN-γ expression in germ-free mice, with levels nearly as high as those in conventional mice (FIG. 6B). Lack of PSA production by the B. fragilis mutant during colonization of germ-free mice resulted in low-level production of T$_H$1 cytokines (FIG. 6B). These results were corroborated by intracellular cytokine staining of splenic lymphocytes from each group, which confirmed that IFN-γ production was attributable to CD4$^+$ T cells (FIG. 6C). The production of IL-2, another T$_H$1 cytokine, by CD4$^+$ T cells in gnotobiotic mice also required PSA production (data not shown).

Together, these results demonstrate that intestinal colonization of germ-free mice by *B. fragilis* alone was sufficient to establish a proper systemic $T_H1/T_H2$ balance within the host—a fundamental aspect of the mammalian immune response.

Example 10

Figure 6D:
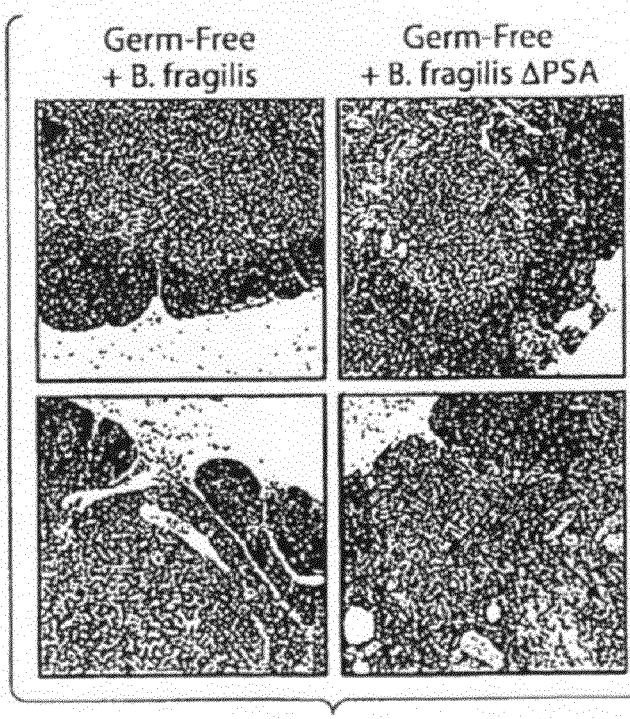
Figure 6E:
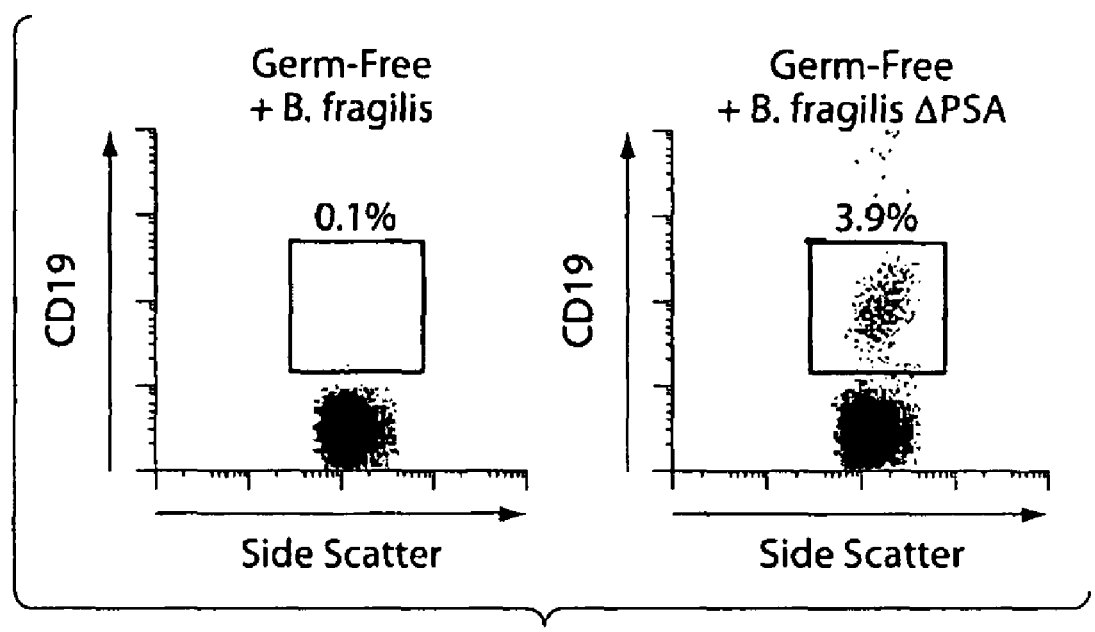

Absence of PSA Production by *B. fragilis* During Colonization is Associated with $T_H2$-Mediated Pathologies of the Thymus Throughout these studies, specimens obtained at necropsy were subjected to histological examination. A rare pathology of the thymus exclusively in mice colonized with *B. fragilis* ΔPSA was noticed. Thymic tissues from germ-free mice colonized with wild-type *B. fragilis* appeared normal, with a darker-staining outer corona and a uniform and homogeneous inner medullary compartment. Surprisingly, at >1 year of age, the majority of mice colonized with *B. fragilis* ΔPSA displayed the outgrowth of B cell-like follicles in the thymic medulla (FIG. 6D). Flow cytometry showed that these tissues contained $CD19^+$ B cells (FIG. 6E) not found in the normal thymus. This rare condition appeared to be similar to human thymic hyperplasia, in which B cells are found in follicles of the medulla (Kasper et al., 2005). The latter condition is associated with numerous autoimmune disorders, most notably myasthenia gravis, a B cell-mediated pathology (Malhotra et al., 1992; Infante and Kraig, 1999). These disorders, as well as B-cell outgrowths, are mediated by overproduction of $T_H2$ cytokines by $CD4^+$ T cells (Zhang et al., 1997; Janeway et al., 2001). It is compelling to speculate that the inability to restore proper $T_H1/T_H2$ balance in germ-free mice through appropriate commensal colonization results in an aberrant $T_H2$ response, which may lead to immune-mediated pathologies.

REFERENCES

Adkins, B. (2000). Development of neonatal Th1/Th2 function. Int Rev Immunol 19, 157-171.

Amsen, D., Blander, J. M., Lee, G. R., Tanigaki, K., Honjo, T., and Flavell, R. A. (2004). Instruction of distinct CD4 T helper cell fates by different notch ligands on antigen-presenting cells. Cell 117, 515-526.

Banchereau, J. and Steinman, R. M. (1998). Dendritic cells and the control of immunity. Nature 392, 245-252.

Bowman, L. M., and Holt, P. G. (2001). Selective enhancement of systemic Th1 immunity in immunologically immature rats with an orally administered bacterial extract. Infect Immun 69, 3719-3727.

Brubaker, J. O., Li, Q., Tzianabos, A. O., Kasper, D. L., and Finberg, R. W. (1999). Mitogenic activity of purified capsular polysaccharide A from *Bacteroides fragilis*: differential stimulatory effect on mouse and rat lymphocytes in vitro. J Immunol 162, 2235-2242.

Cash, H. L., and Hooper, L. V. (2005). Commensal bacteria shape intestinal immune system development. ASM News 71, 77-83.

Cobb, B. A., Wang, Q., Tzianabos, A. O., and Kasper, D. L. (2004). Polysaccharide processing and presentation by the MHCII pathway. Cell 117, 677-687.

Coyne, M. J., Tzianabos, A. O., Mallory, B. C., Carey, V. J., Kasper, D. L., and Comstock, L. E. (2001). Polysaccharide biosynthesis locus required for virulence of *Bacteroides fragilis*. Infect Immun 69, 43424350.

Dobber, R., Hertogh-Huijbregts, A., Rozing, J., Bottomly K., and Negelkerken, L. (1992). The involvement of intestinal microflora in the expansion of $CD4^+$ T cells with a naïve phenotype in the periphery. Dev Immunol 2, 141-150.

Guarner, F., and Malagelada, J. R. (2003). Gut flora in health and disease. Lancet 361, 512-519.

Heufler, C., Koch, F., Stanzl, U., Topar, G., Wysocka, M., Trinchieri, G., Enk, A., Steimman, R. M., Romani, N., and Schuler, G. (1996). Interleukin-12 is produced by dendritic cells and mediates T helper 1 development as well as interferon-gamma production by T helper 1 cells. Eur J Immunol 26, 659-668.

Hooper, L. V., Bry, L., Falk, P. G., and Gordon, J. I. (1998). Host-microbial symbiosis in the mammalian intestine: exploring an internal ecosystem. Bioessays 20, 336-343.

Hooper, L. V., Falk, P. G., and Gordon, J. I. (2000). Analyzing the molecular foundations of commensalism in the mouse intestine. Curr Opin Microbiol 3, 79-85.

Hooper, L. V., and Gordon, J. I. (2001). Commensal host-bacterial relationships in the gut. Science 292, 1115-1118.

Hooper, L. V., Midtvedt, T., and Gordon, J. I. (2002). How host-microbial interactions shape the nutrient environment of the mammalian intestine. Annu Rev Nutr 22, 283-307.

Hooper, L. V. (2004). Bacterial contributions to mammalian gut development. Trends Microbiol 12, 129-134.

Infante, A. J. and Kraig, E. (1999). Myasthenia gravis and its animal model: T cell receptor expression in an antibody mediated autoimmune disease. Int Rev Immunol 18, 83-109.

Janeway, C. A., Travers, P., Walport, M., and Shlomchik, M. (2001). Immunobiology (Garland Publishing).

Kalka-Moll W M, Tzianabos A O, Bryant P W, Niemeyer M, Ploegh H L, and Kasper D. L. (2002). Zwitterionic polysaccharides stimulate T cells by MHC class II-dependent interactions. J Immunol 169, 6149-53.

Kapsenberg, M. L. (2003). Dendritic-cell control of pathogen-driven T-cell polarization. Nat Rev Immunol 3, 984-993.

Kasper, D. L., Braunwald, E., Fauci, A. S., Hauser, S. L., Longo, D. L., and Jameson, J. L. (2005). Harrison's Principles of Internal Medicine (McGraw-Hill Publishing).

Kidd, P. (2003). Th1/Th2 balance: the hypothesis, its limitations, and implications for health and disease. Altern Med Rev 8, 223-246.

Kirjavainen, P. V., and Gibson, G. R. (1999). Healthy gut microflora and allergy: factors influencing development of the microbiota Ann Med 31, 288-292.

Kohm, A. P., Carpentier, P. A., Anger, H. A., and Miller, S. D. (2002). Cutting edge: CD4+ CD25+ regulatory T cells suppress antigen-specific autoreactive immune responses and central nervous system inflammation during active experimental autoimmune encephalomyelitis. J Immunol 169, 4712-4716.

Kononen, E., Jousimies-Somer, H., and Asikainen, S. (1992). Relationship between oral gram-negative anaerobic bacteria in saliva of the mother and the colonization of her edentulous infant. Oral Microbiol Immunol 7, 273-276.

Krinos, C. M., Coyne, M. J., Weinacht, K. G., Tzianabos, A. O., Kasper, D. L., and Comstock, L. E. (2001). Extensive surface diversity of a commensal microorganism by multiple DNA inversions. Nature 414, 555-558.

Macatonia, S. E., Hosken, N. A., Litton, M., Vieira, P., Hsieh, C. S., Culpepper, J. A., Wysocka, M., Trinchieri, G., Murphy, K. M., and O'Garra, A. (1995). Dendritic cells produce IL-12 and direct the development of Th1 cells from naïve $CD4^+$ T cells. J Immunol 154, 5071-5079.

Macpherson, A. J., and Harris, N. L. (2004). Interactions between commensal intestinal bacteria and the immune system. Nat Rev Immunol 4, 478-485.

Macpherson, A. J., and Uhr, T. (2004). Induction of protective IgA by intestinal dendritic cells carrying commensal bacteria. Science 303, 1662-1665.

Malhotra, V., Tatke, M., Khanna, S. K., and Gondal, R. (1992). Thymic histology in myasthenia gravis. Indian J Chest Dis Allied Sci 34, 117-121.

Mowat, A. M. (2003). Anatomical basis of tolerance and immunity to intestinal antigens. Nat Rev Immunol 3, 331-341.

Neurath, M. F., Finotto, S., and Glimcher, L. H. (2002). The role of Th1/Th2 polarization in mucosal immunity. Nat Med 8, 567-573.

Noverr, M. C. and Huffnagle, G. B. (2004). Does the microbiota regulate immune responses outside the gut? Trends Microbiol 12, 562-568.

Pereira, P., Forni, L., Larsson, E., Cooper, M., Heusser, C., and Coutinho, A. (1986). Autonomous activation of B and T cells in antigen-free mice. Eur J Immunol 16, 685-688.

Prescott, S. L., Macaubas, C., Holt, B. J., Smallacombe, T. B., Loh, R., Sly, P. D., and Holt, P. G. (1998). Transplacental priming of the human immune system to environmental allergens: universal skewing of initial T cell responses toward the Th2 cytokine profile. J Immunol 160, 4730-4737.

Rakoff-Nahoum, S., Paglino, J, Eslami-Varzaneh, F., Edberg, S., and Medzhitov, R. (2004). Recognition of commensal microflora by toll-like receptors is required for intestinal homeostasis. Cell 118, 229-241.

Rastall, R. A. (2004). Bacteria in the gut: friends and foes and how to alter the balance. J Nutr 134, 2022S-2026S.

Rescigno, M., Rotta, G., Valzasina, B., and Ricciardi-Castagnoli, P. (2001). Dendritic cells shuttle microbes across gut epithelial monolayers. Immunobiology 204, 572-581.

Rook, G. A., and Brunet, L. R. (2002). Give us this day our daily germs. Biologist (London) 49, 145-149.

Sheikh, A., and Strachan, D. P. (2004). The hygiene theory: fact or fiction? Curr Opin Otolaryngol Head Neck Surg 12, 232-236.

Thery, C., and Amigorena, S. (2001). The cell biology of antigen presentation in dendritic cells. Curr Opin Immunol 13, 45-51.

Trinchieri, G. (2003). Interleukin-12 and the regulation of innate resistance and adaptive immunity. Nat Rev Immunol 3, 133-146.

Tzianabos, A. O., Pantosti, A., Baumann, H., Brisson, J. R., Jennings, H. J., and Kasper, D. L. (1992). The capsular polysaccharide of *Bacteroides fragilis* comprises two ionically linked polysaccharides. Biol Chem 267, 18230-5.

Tzianabos, A. O., Onderdonk, A. B., Rosner, B., Cisneros, R. L., and Kasper, D. L. (1993). Structural features of polysaccharides that induce intra-abdominal abscesses. Science 262, 416-419.

Tzianabos, A. O., Onderdonk, A. B., Zaleznik, D. F., Smith, R. S., and Kasper, D. L. (1994). Structural characteristics of polysaccharides that induce protection against intra-abdominal abscess formation. Infect Immun 62, 4881-4886.

Tzianabos, A. O., Russell, P. R., Onderdonk, A. B., Gibson, F. C., 3rd, Cywes, C., Chan, M., Finberg, R. W., and Kasper, D. L. (1999). IL-2 mediates protection against abscess formation in an experimental model of sepsis. J Immunol 163, 893-897.

Tzianabos, A. O., Finberg, R. W., Wang, Y., Chan, M., Onderdonk, A. B., Jennings, H. J., and Kasper, D. L. (2000). T cells activated by zwitterionic molecules prevent abscesses induced by pathogenic bacteria. J Biol Chem 275, 6733-40.

Tzianabos, A. O., and Kasper, D. L. (2002). Role of T cells in abscess formation. Curr Opin Microbiol 5, 92-96.

Umetsu, D. T., McIntire, J. J., Akbari, O., Macaubas, C., and DeKruyff, R. H. (2002). Asthma: an epidemic of dysregulated immunity. Nat Immunol 3, 715-720.

Von Hertzen, L. C., and Haahtela, T. (2004). Asthma and atopy—the price of affluence? Allergy 59, 124-137.

Yamanaka, T., Helgeland, L., Farstad, I. N., Fukushima, H., Midtvedt, T., and Brandtzaeg, P. (2003). Microbial colonization drives lymphocyte accumulation and differentiation in the follicle-associated epithelium of Peyer's patches. J. Immunol. 170, 816-22.

Zhang, G. X., Navikas, V., and Link, H. (1997). Cytokines and the pathogenesis of myasthenia gravis. Muscle Nerve 20, 543-551.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

We claim:

1. A method of promoting immune system maturation in an infant, comprising
    enterally administering to the infant an effective amount of a nutritional formula or nutritional supplement composition, said composition comprising an isolated zwitterionic polysaccharide consisting essentially of repeating units, wherein each repeating unit comprises
    two to ten monosaccharides, and
    a free amino moiety and a negatively charged moiety selected from the group consisting of carboxylate, phosphate, phosphonate, sulfate, and sulfonate.

2. The method of claim 1, wherein the zwitterionic polysaccharide is a naturally occurring bacterial capsular polysaccharide.

3. The method of claim 1, wherein the zwitterionic polysaccharide is a *B. fragilis* capsular polysaccharide A (PSA).

4. The method of claim 3, wherein the PSA is PSA1.

5. The method of claim 3, wherein the PSA is PSA2.

6. The method of claim 1, wherein the zwitterionic polysaccharide is a *B. fragilis* capsular polysaccharide B (PSB).

7. The method of claim 1, wherein the zwitterionic polysaccharide is selected from the group consisting of *Shigella sonnei* Phase I lipopolysaccharide 0-antigen, *Streptococcus pneumoniae* type 1 capsular polysaccharide, and *Streptococcus pneumoniae* group antigen C substance.

8. The method of claim 1, wherein the nutritional formula or nutritional supplement is a nutritional formula.

9. The method of claim 1, wherein the nutritional formula or nutritional supplement is a nutritional supplement.

10. The method of claim 1, wherein the enterally administering is orally administering.

11. The method of claim 1, wherein the infant is 0-6 months old.

12. The method of claim 1, wherein the immune system maturation is an increase in a T helper 1 marker to a T helper 2 Marker.

13. The method of claim 12, wherein the T helper 1 marker is a cytokine selected from interferon gamma (IFN-y) and interleukin 2 (IL-2).

14. The method of claim 12, wherein the T helper 2 marker is a cytokine selected from interleukin 4 (IL-4) and interleukin 5 (IL-5).

\* \* \* \* \*